US007101669B2

(12) United States Patent
Thompson et al.

(10) Patent No.: US 7,101,669 B2
(45) Date of Patent: Sep. 5, 2006

(54) ENZYME-BASED REGENERATION OF SURFACE-ATTACHED NUCLEIC ACIDS

(75) Inventors: Michael Thompson, Toronto (CA); Linda Michelle Furtado, Scarborough (CA)

(73) Assignee: Sensorchem International Corporation, Toronto (CA)

( * ) Notice: Subject to any disclaimer, the term of this patent is extended or adjusted under 35 U.S.C. 154(b) by 357 days.

(21) Appl. No.: 10/240,932

(22) PCT Filed: Apr. 12, 2001

(86) PCT No.: PCT/CA01/00500

§ 371 (c)(1),
(2), (4) Date: Jul. 14, 2003

(87) PCT Pub. No.: WO01/79535

PCT Pub. Date: Oct. 25, 2001

(65) Prior Publication Data

US 2004/0101838 A1 May 27, 2004

(30) Foreign Application Priority Data

Apr. 12, 2000 (CA) .................................. 2302827

(51) Int. Cl.
*C12Q 1/68* (2006.01)
*C07H 21/02* (2006.01)
*C07H 21/04* (2006.01)

(52) U.S. Cl. ..................... 435/6; 536/23.1; 536/24.3
(58) Field of Classification Search .................. 435/6; 536/23.1, 24.3
See application file for complete search history.

(56) References Cited

U.S. PATENT DOCUMENTS

| 4,999,284 | A | | 3/1991 | Ward et al. | |
|---|---|---|---|---|---|
| 5,374,521 | A | | 12/1994 | Kipling et al. | |
| 5,501,986 | A | | 3/1996 | Ward et al. | |
| 5,518,900 | A | | 5/1996 | Nikiforov et al. | |
| 5,849,486 | A | | 12/1998 | Heller et al. | |
| 5,880,552 | A | | 3/1999 | McGill et al. | |
| 6,017,696 | A | | 1/2000 | Heller | |
| 6,087,112 | A | * | 7/2000 | Dale | 435/6 |
| 6,232,066 | B1 | * | 5/2001 | Felder et al. | 435/6 |
| 2003/0054388 | A1 | * | 3/2003 | Garner et al. | 435/6 |
| 2004/0033525 | A1 | * | 2/2004 | Monforte et al. | 435/6 |

FOREIGN PATENT DOCUMENTS

| CA | 2271179 | 11/2000 |
|---|---|---|
| EP | 0578138 | 1/1994 |
| WO | WO99/20640 | 4/1999 |
| WO | WO00/68419 | 11/2000 |

OTHER PUBLICATIONS

Kazunori Okano, et al., DNA Probe Assay Based on Exonuclease III Digestion of Probes Hybridized on Target DNA, *Analytical Biochemistry*, 288, pp. 101-108, 1995, XP-002211015.

Russell G. Higuchi, et al, "Production of single-stranded DNA templates by exonuclease digestion following the polymerase chain reaction", *Nucleic Acids Research*, 17, Oct. 11, 1989, No. 19, XP-000226748.

Matthew Reason, et al., "Characterisation of fatty acid multilayers using a TSM biosensor", *Int. J. of Pharmaceutics*, 195, 2000, pp. 25-28, XP-002211016.

Francesco Ferrante, et al. "Molecular slip at the solid-liquid interface of an acoustic-wave sensor", *Journal of Applied Physics*, 76, No. 6, Sep. 15, 1994, pp. 3448-3462, XP-000470063.

Jorg D. Hoheisel, "On the Activities of *Escherichia coli* Exonuclease III", *Analytical Biochemistry*, 209, pp. 238-246, 1993, XP-002211017.

* cited by examiner

*Primary Examiner*—Ethan Whisenant
(74) *Attorney, Agent, or Firm*—Kathleen E. Marsman; Borden Ladner Gervais LLP

(57) ABSTRACT

Enzyme-based regeneration of surface-attached nucleic acids is described herein. Microarrays involving hybridization of a probe to a target are important tools for genetic analysis. Conventionally, a microarray is used for a single analysis, after which it is discarded. The invention relates to a process for regeneration of a microarray through enzymatic digestion of a target from a surface-attached probe using a nuclease to digest a single strand of a nucleic acid duplex with directional specificity starting from the free end of the target strand. For example, a probe oligonucleotide bound to a gene chip at the 5'-end hybridizes to a target nucleic acid, leaving the 5' end of the target open to 5'–3' digestion. Lambda-exonuclease (λ-exonuclease) cleaves single nucleotides from the 5' end of a duplex, progressing in the 5'–3' direction. Once the target strand is digested, the enzyme is rinsed from the microarray. The microarray is thus regenerated and ready for a subsequent use.

10 Claims, 15 Drawing Sheets

SEQUENCE LISTING

<160> NUMBER OF SEQ ID NOS: 15

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: F1 probe
      oligonucleotide has 5' biotin attachment

<400> SEQUENCE: 1
tataaaaaga gagagagatc gagtc                                          25

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: F2 target
      oligonucleotide is complementary to F1

<400> SEQUENCE: 2
gactcgatct ctctctcttt ttata                                          25

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: F2-T4C
      target oligonucleotide differs from F2 in that C is
      substituted for T at position 22

<400> SEQUENCE: 3
gactcgatct ctctctcttt tcata                                          25

```
<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: F2-T4G
      target oligonucleotide differs from F2 in that G is
      substituted for T at position 21

<400> SEQUENCE: 4
gactcgatct ctctctcttt tgata                                    25

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence:  F2-C13A
      target oligonucleotide differs from F2 in that A
      is substituted for C at position 13

<400> SEQUENCE: 5
gactcgatct ctatctcttt ttata                                    25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: F2-C13T
      target oligonucleotide differs from F2 in that T is
      substituted for C at position 13

<400> SEQUENCE: 6
gactcgatct ctttctcttt ttata                                    25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence:  F2-T14C
      target oligonucleotide differs from F2 in that C
      is substituted for T at position 12

<400> SEQUENCE: 7
gactcgatct ccctctcttt ttata                                    25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: F2-T14A
      target oligonucleotide differs from F2 in that A is
      substituted for T at position 12

<400> SEQUENCE: 8
gactcgatct cactctcttt ttata                                    25

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: F2-C21A
      target oligonucleotide differs from F2 in that A is
      substituted for C at position 5
```

```
<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence:

<400> SEQUENCE: 9
gactagatct ctctctcttt ttata                                              25

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: F2-C21T
      target oligonucleotide differs from F2 in that T is
      substituted for C at position 5

<400> SEQUENCE: 10
gacttgatct ctctctcttt ttata                                              25

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: X-F2
      oligonucleotide has a segment of 11 bases and a
      segment of 5 bases which are complementary to F1

<400> SEQUENCE: 11
atatttttct ctctctctag ctca                                               24

<210> SEQ ID NO 12
<211> LENGTH: 11
<212> TYPE: DNA
<213> ORGANISM: Artificial Sequence
<220> FEATURE:
<223> OTHER INFORMATION: Description of Artificial Sequence:  "73%"
      oligonucleotide has one segment of 4 bases and one
      segment of 3 bases complementary to F1

<400> SEQUENCE: 12
atctcgcgtc t                                                             11

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: MN-F2
      target oligonucleotide is non-complementary to F1

<400> SEQUENCE: 13
tcagatcgag agagagaggg ggcgc                                              25

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: F3 probe
      oligonucleotide has 5' biotin attachment

<400> SEQUENCE: 14
cgtacggatc acagatgcag tacgc                                              25

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: F4 target
```

-continued oligonucleotide is complementary to F3

<400> SEQUENCE: 15
gcgtactgca tctgtgatcc gtacg                                        25

ENZYME-BASED REGENERATION OF SURFACE-ATTACHED NUCLEIC ACIDS

FIELD OF THE INVENTION

This invention relates to nucleic acid reactions, and to processes for the biochemical detection and analysis of nucleic acids. More specifically, it relates to hybridization of probe and target nucleic acid in analysis and detection processes using microarrays, also known as "gene chips", and to removal of a target strand from a surface-attached probe.

BACKGROUND OF THE INVENTION

The process of hybridization of nucleic acids and is the formation of double stranded nucleic acids from single stranded nucleic acids, by specific interaction of complementary base pairs on the respective nucleic acid strands. Nucleic acids are long chain molecules made up of the nucleosides adenosine (A), guanosine (G), cytidine (C), and thymidine (I) in DNA or uridine (U) in RNA, covalently linked by phosphate ester linkages between the 3'-hydroxyl group on the sugar residue of one nucleoside and the phosphate linked to the 5' position of the adjacent nucleoside, in various sequences. There is chemical affinity between respective pairs of purine and pyrimidine bases comprising part of each nucleotide unit (T-A and C-G). Hybridization thus requires the presence of complementary sequences of bases in nucleic acids, and is an extremely specific and sensitive reaction. It is the basis of oligonucleotide and DNA/RNA microarrays, such as biosensors, genosensors, or gene chips, being developed for use in the areas of genetic testing and sequencing, and drug discovery and development.

A critical component in obtaining genetic information is the ability to screen a DNA sequence. The microarray is a device which allows small scale and relatively high throughput nucleic acid analysis. Microarray analysis represents an aggregation of technologies, such as sequencing by hybridization (SBH), light-directed, spatially addressable interrogation, combinatorial chemical synthesis, confocal fluorescence microscopy, robotic spotting and polymerase chain reaction (PCR). These technologies offer significant advantages in terms of the avoidance of time-consuming protocols through the use of highly multiplexed analyses of DNA sequences.

The principle of SBH is based on the fact that a solution of digested linear DNA sequence incorporating the four bases is composed of overlapping shorter sequences. Accordingly, SBH employs hybridization of a set of single strand oligonucleotides or DNA with sub-sequences in a particular DNA fragment. In practical terms, the DNA target labelled with fluorescent tagging agents is allowed to interact with probes, which are attached to a substrate surface such as glass. Detection of the level of hybridization is effected using confocal fluorescence microscopy.

Microarrays are devices involving the attachment or immobilization of a known nucleic acid sequence (or "probe") on a surface. Sensors for the detection of hybridization can be constructed from acoustic wave, optical and electrochemical devices. Detection of binding of a target nucleic acid from a test sample is effected by various methods such as radiolabelling, fluorescence or confocal microscopy. Once they have been exposed to the target (oligo)nucleic acids, some or most of the probes are hybridized as double-stranded nucleic acid or oligonucleotides.

Conversion of double stranded nucleic acid to single stranded nucleic acid (denaturation) takes place relatively easily in aqueous solution using conventional methods such as heating, exposure to very high pH, of by using chemical denaturation, for example by exposure to urea. Different considerations apply to immobilized nucleic acid probes. Heating and chemical reagents have proven unsuccessful in the concurrent denaturation of double stranded DNA and regeneration of the surface-attached probe for re-use of the microarray. Accordingly, conventional microarrays are used once for a hybridization analysis and discarded thereafter. This makes microarray analysis of nucleic acids very expensive.

There are two methods for the fabrication of nucleic acid microarrays. The first involves the use of directed light via a combination of photolithography with combinatorial chemical synthesis. Bases are gradually added to a surface in a linear sequence by a photolithographical stepwise process, which includes the use of photolabile protecting moieties. Such a protocol can produce many thousands of probe nucleic acid sequences (approximately 20-mers) on a substrate surface on which the exact location of a particular probe is know accurately. The second approach involves attachment of a probe nucleic acid sequence by robotic spotting of the probe onto the surface of a substrate.

The pervasive strategy for the practical use of nucleic acid microarrays to date has been to discard the microarray after a single analysis. There are two significant disadvantages to this approach. First, despite much promise to the contrary, microarrays are still expensive to produce and purchase. Accordingly, if multiple analyses are to be performed on a particular sample the whole protocol becomes inordinately expensive. Second, particularly with respect to microarrays generated by robotic spotting of a probe onto a surface, it has proven difficult to produce identical microarrays that yield highly reproducible analytical results. Considerable variety in the pattern of probe density is often experienced leading to irreproducibility.

SUMMARY OF THE INVENTION

It is an object of the present invention to obviate or mitigate at least one disadvantage of previous processes and systems methods for microarray analysis of nucleic acids.

The invention provides a process for removing a target nucleic acid from a duplex formed by hybridization of the target nucleic acid with a probe nucleic acid, the probe nucleic acid having a surface-attached end. The process comprises the following steps: a) exposing the duplex to a nuclease for a period of time adequate to digest the target nucleic acid, the nuclease having activity for digesting one strand of a duplex in a direction starting from an end of the target nucleic acid opposite to the end hybridized to the surface-attached end of the probe nucleic acid; and b) rinsing the nuclease from the probe nucleic acid.

Further, the invention provides a process for regenerating a microarray having a probe hybridized to a target, the probe having a surface-attached end at which the probe is attached to the microarray. The process comprises the steps of: a) digesting the target with a nuclease having activity for digesting one strand of a double-stranded nucleic acid in a direction starting from an end of the target opposite the end hybridized to the surface-attached end of the probe; and b) rinsing the nuclease from the microarray.

The invention also relates to a re-usable microarray system comprising a microarray surface, a probe nucleic acid attached to the surface in a pre-determined orientation for hybridizing to a target nucleic acid from a test sample, the pre-determined orientation being selected from 3' end attachment and 5' end attachment, and a nuclease having activity for digesting one strand of a double-stranded nucleic acid in a direction starting from a free end of said target nucleic acid so as to remove a hybridized target nucleic acid from the probe nucleic acid while leaving the probe nucleic acid intact on the microarray surface.

Additionally, the invention relates to a re-usable microarray kit comprising: a) a microarray having a surface, a probe nucleic acid attached to the surface in a pre-determined orientation for hybridizing to a target nucleic acid from a test sample, the pre-determined orientation being selected from 3' end attachment and 5' end attachment; and b) a nuclease having activity for digesting one strand of a double-stranded nucleic acid in a direction starting from a free end of the target nucleic acid so as to remove a hybridized target nucleic acid from the probe nucleic acid while leaving the probe nucleic acid intact on the microarray surface.

According to an embodiment of the invention, there is provided a use of lambda-exonuclease for removing a target nucleic acid from a duplex comprising a target nucleic acid and a surface-attached probe nucleic acid.

Advantageously, this invention addresses concerns of cost and reproducibility through regeneration of microarrays for use in more that one analysis. By using enzymatic digestion to effect the required removal or "melting" of a single strand of nucleic acid from a duplex present on a microarray surface after use, problems arising from harsh conventional methods of de-hybridization are traversed. The use of higher temperatures or chemical agents to melt double stranded nucleic acids can damage a microarray or the individual microarray components, either the substrate surface or the probe strands attached to the surface. However, by using an enzymatic process for removal of a target nucleic acid from a probe, the enzyme allows selective removal of the target strand, leaving the probe strand and substrate surface intact, generally undamaged, and available for re-use.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein.

DETAILED DESCRIPTION

Figure 1:
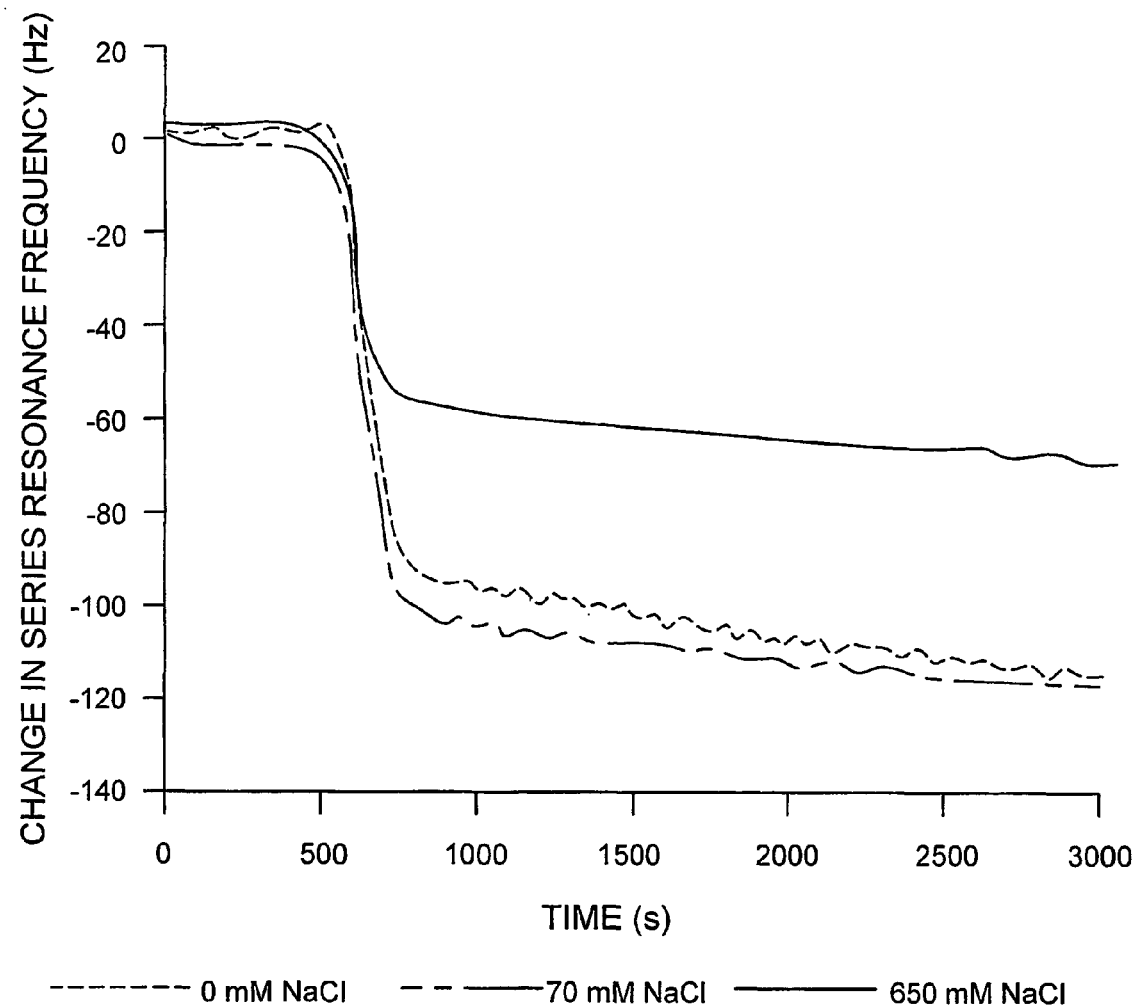
FIG. 1 shows the response of 9 MHz TSM sensor with a polished gold electrode to avidin (10 mg/ml) in various concentrations of electrolyte. NaCl concentrations of 0, 70, and 650 mM are shown.

This invention relates to a method for regeneration of a nucleic acid microarray. A microarray is formed in a conventional manner having a substrate surface to which target nucleic acid strands are attached. The microarray is then reacted with a test sample containing a target nucleic acid of interest in single strand form in order to effect hybridization under appropriate conditions. As with conventional microarrays, a detection method such as fluorescence confocal microscopy can be employed to detect the intensity and location of zones of duplex formation, indicative of target hybridization to the probe. Following hybridization of the target to the probe, the microarray is treated with a nuclease, such as a deoxyribonuclease enzyme in order to remove the target nucleic acid from the probe, thereby returning any double-stranded zones to single-stranded probes. After washing to remove the enzyme, the microarray can be used again instead of being disposed of. This leads to a cost saving in addition to the potential for increased reproducibility for a particular analysis.

The invention involves denaturation of a double stranded nucleic acid resulting from microarray testing, consisting of a probe nucleic acid strand and a target nucleic acid strand hybridized thereto, by treatment with an enzyme which is selective for digestion of one strand of double stranded DNA in either the 5'–3' direction or the 3'–5' direction. One of the ends of the probe nucleic acid strand is blocked from enzyme activity through its attachment to the substrate surface either directly via an immobilizing linker, or indirectly by chemical blocking or a detection group. The reverse end of the target strand hybridized to the probe (opposite to the surface-attached end of the probe) is free and available to a nuclease enzyme specific for digestion of nucleic acid in the direction starting from the free end of the target strand. Thus, the nuclease enzyme will digest the target strand but leave the probe strand intact, and still blocked from enzymatic digestion due to its attachment to the substrate surface. As a result, a microarray with the original probe strand is restored, for re-use in another probe-target hybridization assay.

The term "nucleic acid", either singular or plural, as used herein means DNA or RNA, either as individual nucleic acids (ACGT or U) or as strands of two or more individual nucleic acids, either as oligonucleotides or longer sequences which may be full length or partial sequence of RNA such as mRNA, cDNA, genomic or mitochondrial DNA. Single-stranded (ss) and double stranded (ds) nucleic acids may be referred to as nucleic acid(s).

As referred to herein, the term "microarray" either singular or plural means a device comprising a surface on which one or more nucleic acid is attached. A microarray may have one specific nucleic acid strand (or "probe" strand) bound thereto in a plurality of locations or may have different nucleic acid strands bound to the surface in predetermined locations. The surface of the microarray should be understood to mean any type of surface which is amenable to attachment of a nucleic acid. Examples of microarray surfaces include but are not limited to such surfaces as a multi-well plate, a glass slide, a single crystal or a plurality of crystals, a metal surface, a polymeric surface, or a ceramic surface. The nucleic acid may be attached to the surface in any manner acceptable in the art. The terms biosensor, gene chip, genosensor, and nucleic acid array are considered to refer to types of microarrays.

By the term "regeneration" as used herein to refer to microarrays, it is meant removal or "de-hybridization" of a significant portion of a hybridized nucleic acid, for example from a test sample, from the surface-attached probe strand on a microarray. The regeneration involves removal of the entire test strand or a portion thereof in an amount adequate to allow the microarray to be re-used for hybridization with nucleic acids in a subsequent test sample. If a plurality of probes are present on a microarray, having either the same sequence or different sequences, the microarray can be said to be "regenerated" if the hybridized nucleic acid strands from the test sample can be removed from the probe stands to an extent adequate to allow re-use of the microarray. For example, it is possible that some test sample nucleic acid strands remain hybridized in full or in part to the probe strands, provided that an adequate number of probe strands are available for re-use.

Nuclease. The term "nuclease" as used herein refers to a nuclease capable of digesting RNA (ribonuclease) or DNA (deoxyribonuclease) in a manner appropriate for use with the invention. The desired functional activities of the nucleases for use with the invention are delineated below.

The nuclease for digestion of the target strand component of the target/probe duplex according to the invention is capable of digesting a single strand of a duplex (or double-stranded) nucleic acid in either the 5'–3' direction or in the 3'–5' direction, depending on the orientation of the probe strand as it is attached to the surface. For example, if the probe is attached to the surface at the 5' end, the 3' end of the target nucleic acid will hybridise to the surface-attached end of the probe. Thus, the 5' end of the target nucleic acid will be free and accessible to enzymatic degradation. The nuclease cannot access the 5' end of the probe to digest the probe strand, since this end of the probe is obscured by its surface attachment. Conversely, if the probe is attached to the surface at the 3' end, the nuclease enzyme to be used in the inventive process is one capable of digesting a single strand of nucleic acid from a duplex starting at the 3' end. In this way, only the target strand can be digested from the duplex.

In living organisms, enzymes are used to digest or "melt" dsDNA for replication and repair. Nuclease specific for digestion of a single strand of duplex DNA in a direction-specific manner are known. However, these enzymes require access to the appropriate end of a duplex DNA. In assays conducted in vitro, bulk solutions of double stranded DNA can be digested using nucleases, and the kinetics are such that collisions occur regularly between the enzyme and the duplex. Problems are inherent in digestion of a single stranded region of a surface-attached duplex include reduced numbers of collisions compared to use of the enzyme in bulk solution to digest mobile duplexes. However, the invention disclosed herein provides a process for applying nuclease to a surface-attached duplex, having the desirable outcome that the surface-attached probe strand remains intact. According to an embodiment of the invention, the enzyme Lambda-exonuclease (λ-exonuclease) is used to digest a target nucleic acid strand (DNA) from the probe strand, which remains attached to the surface and can be used for further analysis, after appropriate washing to remove the enzyme.

An example of a suitable enzyme for use in the invention is λ-exonuclease, a deoxyribonuclease capable of digesting a strand of target DNA because it is specificity for 5'–3' direction of digestion. When a probe is attached to the substrate surface via the 5' end, digestion of the probe will not occur because the 5' end thereof is unavailable to λ-exonuclease. Accordingly in this embodiment of the invention, λ-exonuclease can be used to restore a microarray having a 5' attached probe to a single-stranded state for re-use.

According to another embodiment of the invention, the probe is attached to the substrate surface at its 3' end, so that the 5' end of the probe strand is free in solution. In this embodiment, an enzyme which is specific for digestion of one strand of double stranded DNA in the 3'–5' direction can be used for specific digestion of the target strand and restoration of the probe for re-use. An example of such an enzyme is the exodeoxyribonuclease exonuclease III.

Enzymes to be used in optional pre-treatment steps may also be nucleases having a specific activity as outlined below.

Pretreatment. According to the invention, it may be desirable to pretreat the hybridized duplex formed between the probe and the target, particularly when non-duplex regions exist in the target strand. For example, in test samples having a target which is considerably longer strand than the probe, removal of single-stranded regions of the target may more effectively prepare the duplex for digestion of the target with the nuclease, for example if the nuclease has better activity with blunt ended duplexes. Such pretreatment can be effected using a preparatory enzyme, such as exonuclease VII or Mung Bean nuclease, each of which is capable of digesting single-stranded nucleic acids while leaving duplex regions intact. A preparatory enzyme having directional-specific activity in the requisite direction, so as to only act on the unbound end of the target strand may be used.

In cases where the hybridized probe-target duplexes are not blunt-ended, it may be beneficial to use one or more other deoxyribonucleases prior to or in combination with the target digesting nuclease, to prepare the duplex in blunt-ended form for action by the nucleases. Exonuclease VII is an exodeoxyribonuclease which digests single-stranded DNA from both the 3' and 5' ends, and could be used to cleave from 3' and 5' ends in situations where the target nucleic acid is considerably longer than the probe nucleic acid. Mung Bean nuclease is a single-stranded nuclease which digests single-stranded DNA or RNA but which leaves duplex regions intact. Mung Bean nuclease could also be used to prepare a microarray exposed to a sample in such situations wherein the DNA in the sample is considerably longer than the probe, which may be an oligonucleotide ranging from, for example, 10 to 30 bases in length.

Surface-Attachment of Probe to Microarray. The re-usable microarray system according to the invention involves the surface-attachment of the probe nucleic acid strand. The attachment of the probe to the surface of the microarray can be achieved through any acceptable means provided that the attached probe end is rendered inaccessible to enzyme degradation by the nuclease. By the term "attachment" or "surface-attached", it is meant any direct or indirect means of immobilization that renders the probe attached to a surface in either a covalent or non-covalent manner. Conventional means of surface attachment include the presence of a chemical blocking group between the probe strand and the surface of the microarray, an immobilization support or ligand or any combination of these. Many such methods of surface attachment are known in the art. For example, a neutravidin/biotin system of attachment may be used, as described herein. Further, attachment may be accomplished as described in Canadian Application No. 2,306,631, entitled "High surface density covalent immobilization of oligonucleotide monolayers" published on Apr. 29, 1999, which describes immobilization of a biomolecule, via a terminal thiol group, to a substrate having surface hydroxyl groups and a detection molecule.

Commonly, nucleic acids for use in microarrays are modified at the 5' end, for example by biotinylation and/or by direct attachment to the substrate surface at the 5' end. This leaves the 3' end exposed to the test sample containing the target nucleic acid. The target nucleic acid from the test sample hybridizes to the probe in a head-to-tail manner, in this case with its 5' end exposed to the test sample.

The material from which the surface is made can be any surface amenable to probe attachment. Advantageously, the invention may be used with temperature-sensitive or chemical-sensitive surfaces, since the use of enzymatic activity to "melt" duplex DNA is less harsh than other methods of de-hybridization.

Applications to Biosensor Microarrays. The re-usable microarray according to the invention may be a biosensor, such as a TSM (transverse shear mode) sensor. Because the inventive microarray is re-usable, the incorporation of the invention in a biosensor is particularly advantageous because the standardization and measurements used in such a biosensor can be retained from run-to-run, as the particular device is re-used. Thus, more sensitive and accurate measurements can be obtained. Biosensors known in the art, such as those disclosed in U.S. Pat. No. 5,374,521 entitled "Acoustic reflection process for molecular sensing using a bulk acoustic wave quartz sensor" issued on Dec. 20, 1994, and in International Patent Application No. PCT/CA00/00504, published as WO 00/68419 on Nov. 16, 2000, entitled "Apparatus and process for monitoring and detecting small molecule-biomolecule interactions".

The method according to the invention can be applied to low-density or high-density oligonucleotide and DNA microarrays. Applications of such re-usable microarray systems include multi-use nucleic acid detection microarrys, for quantitative or qualitative determinations. Further, the method may be used for specific removal of a nucleic acid from a sample, and in this way can be regenerated, similar to a purification column. When the microarray is a biosensor, the quality of the binding of the target to a surface-attached probe can also be determined. For example, if a nucleotide is missing or substituted in a target sequence in a sample, the affinity with which the target binds to the probe can be detected. Nucleotide polymorphisms related to disease states can thus be detected through assessment of the quality of binding between the probe and the target. Advantageously, the same microarray can be used to compare a test sample with a standard because of the ability of the microarray to be regenerated according to the invention.

EXAMPLES

The invention is further described, for illustrative purposes, in the following specific Examples. General methodology having application to all examples is described herein below.

Reagents. All reagents were freshly prepared from the specified commercial product without further treatment. ImmunoPure™ neutravidin was purchased from Chromatographic Specialities (Brockville, ON, Canada). The A, G, C and T CPG columns and phosphoramidites and biotin phosphoramidite were purchased from Applied Biosystems and BioCan Scientific. The reagents for the DNA/RNA synthesizer: tetrazole/acetonitrile; 1-methylimidazole/THF; acetic anhydride/pyridine/THF; iodine/water/pyridine/THF; and anhydrous acetonitrile were purchased from Applied Biosystems and aqueous ammonia was purchased from Sigma-Aldrich Canada. Aqueous ammonia, trifluoroacetic acid, and acetonitrile used for purification were obtained from Sigma-Aldrich and prepared in the appropriate concentrations by dilution with deionized water. Triethylammonium acetate (TEAA) for purification was made from glacial acetic acid and triethylamine (Sigma-Aldrich) and deionized water.

A buffer solution of 10 mM Tris-HCl (Canadian Life Technologies), 70 mM NaCl and 0.2 mM EDTA (Sigma-Aldrich) was used to prepare neutravidin and oligonucleotide solutions for experiments. A buffer solution of 67 mM Glycine-KOH (Sigma-Aldrich), and 2.5 mM $MgCl_2$ (Sigma-Aldrich) and pH 9.4 was used to prepare oligonucleotide and λ-exonuclease for experiments. Lambda exonuclease was purchased from Canadian Life Technologies (product #28023-018). [γ-$^{32}$P] ATP was purchased from Mandel Scientific Company Ltd. (product NEG 502Z). 10×T4 PNK reaction buffer (contains Tris-HCl, $MgCl_2$, dithiothreitol) and T4 Polynucleotide Kinase were purchased from New England Biolabs. Solutions of 3N NaOAc and phenol/chloroform/isoamyl alcohol were prepared from reagents purchased from Sigma-Aldrich. CHROMATIDE Alexa Fluor 546-14 dUTP (product #C-11401) and CHROMATIDE BODIPY 630/650 dUTP (product #C-11395) were purchased from Molecular Probes Inc. The labelling kits (including 10×NE Reaction Buffer, $CoCl_2$, and deoxynucleotidyl transferase) were purchased from New England Biolabs Ltd. (3-mercaptopropyl)-trimethoxysilane, aqueous ammonia, anhydrous ethanol, and acetic acid were purchased from Sigma-Aldrich Canada and used as received. Sodium bicarbonate/sodium carbonate (500 mM, pH 9.0) was prepared from chemicals purchased from Sigma-Aldrich. Tween 20 was purchased from Sigma-Aldrich.

Non-biotinylated, 5'-thiol-modifed-F1, 3'-biotin-F1, F2 and MN-F2 used for $^{32}$P labelling and/or fluorophore labelling for radiochemical and fluorescent analysis, as well as F3 and F4, were synthesized by the Centre for Applied Genomics, The Hospital for Sick Children, Toronto, ON, Canada. The purified sequences were freeze-dried and stored at 4° C. until required. Biotin-TAR RNA and $Tat_{12}$ peptide were provided by Parke-Davis pharmaceutical research, Ann Arbor, Mich., USA.

Oligonucleotide Synthesis. Oligonucleotides were synthesized for this research, and were all freeze- or vacuum-dried and stored at 4° C. until required. F1 has a thiol modifier in place of biotin for immobilization on glass slides. In the sequences below, bases shown in bold and underlined are altered from the sequence F2. Bases italicized and/or underlined are regions complementary to segment(s) of F1

```
F1:
5'-biotin-TATAAAAAGAGAGAGAGATCGAGTC-3'    SEQ ID NO:1

F2:
5'-GACTCGATCTCTCTCTCTTTTTATA-3'           SEQ ID NO:2

F2-T4C:
5'-GACTCGATCTCTCTCTCTTTTCATA-3'           SEQ ID NO:3

F2-T4G:
5'-GACTCGATCTCTCTCTCTTTTGATA-3'           SEQ ID NO:4

F2-C13A:
5'-GACTCGATCTCTATCTCTTTTTATA-3'           SEQ ID NO:5

F2-C13T:
5'-GACTCGATCTCTTTCTCTTTTTATA-3'           SEQ ID NO:6

F2-T14C:
5'-GACTCGATCTCCCTCTCTTTTTATA-3'           SEQ ID NO:7

F2-T14A:
5'-GACTCGATCTCACTCTCTTTTTATA-3'           SEQ ID NO:8

F2-C21A:
5'-GACTAGATCTCTCTCTCTTTTTATA-3'           SEQ ID NO:9

F2-C21T:
5'-GACTTGATCTCTCTCTCTTTTTATA-3'           SEQ ID
                                          NO:10

X-F2:
5'-ATATTTTTCTCTCTCTCTAGCTCA-3'            SEQ ID
                                          NO:11

"73%":
5'-ATCTCGCGTCT-3'                         SEQ ID
                                          NO:12

MN-F2:
5'-TCAGATCGAGAGAGAGAGGGGGCGC-3'           SEQ ID
                                          NO:13

F3:
5'-biotin-CGTACGGATCACAGATGCAGTACGC-3'    SEQ ID
                                          NO:14

F4:
5'-GCGTACTGCATCTGTGATCCGTACG-3'           SEQ ID
                                          NO:15
```

Materials and Apparatus. Poly-pak ion exchange columns used for the purification of synthesized nucleic acids were purchased from BioCan Scientific. Centri-Sep purification columns (Princeton Separations Inc.) were used according to the accompanying protocol. The optically polished 9 MHz AT-cut piezoelectric quartz crystals with gold electrodes were purchased from International Crystal Manufacturing Inc. Glass slides were purchased from Sigma-Aldrich Canada (product #S 8400).

The crystal was assembled within a TSM sensor flow cell in a configuration employed for both the introduction of reagents and TSM measurement in a flow-through manner. The Plexiglas cell has two halves separated by O-rings. One face of the crystal was in contact with both flowing and static aqueous solutions, while the other face was kept under nitrogen. Temperature was controlled through a Hybaid Micro-4 hybridization oven (HB-MCR4, InterScience, Markham, ON, Canada) and measured by a mercury thermometer. Flow-through experiments were performed using a 4-channel EVA-pump Model 1000 peristaltic pump (Eppendorf) which was adapted and combined with an EVA-Valve Model 2000 injector valve (Eppendorf). The PTFE tubing for the sample loop had an inner diameter of 0.5 mm, while all the other tubings had an internal diameter of 0.8 mm. Finally, the TSM responses in liquid were measured by an HP 4195A network/spectrum analyzer (Hewlett-Packard). The values of the equivalent circuit were calculated internally by the analyzer from measured data. The calibration of the network analyzer at a centre frequency of 9 MHz was accomplished using a pre-set calibration program. The analyzer scanned 401 points about a centre frequency of 9 MHz (with 120 kHz bandwidth). The system was set, by user input, to record the acquired data every 30 seconds.

Contact angle measurements were obtained using a goniometer, courtesy of Dan Kwok, Dept. of Engineering, University of Toronto. X-ray photoelectron spectroscopy (XPS) spectral data were obtained with a Leybold MAX 200 XPS (Leybold, Cologne, Germany) instrument using an unmonochromatized Mg Kα source and an analysis area of 2×4 $mm^2$. Survey and low resolution spectra were obtained using a pass energy of 192 eV; high resolution spectra were acquired with a pass energy of 48 eV. All spectra were satellite-subtracted and normalized using software and elemental sensitivity factors provided by the manufacturer. The binding energy scale was further calibrated to 285.0 eV for the main C (1s) feature in order to compensate for sample charging effects.

Radiochemical counting of solutions containing $^{125}$I-labelled $Tat_{12}$ and $^{32}$P-labelled B-TAR and devices coated with these species was accomplished using a Riastar 103271 γ-ray detector (Hewlett-Packard) and a 1219 Rackbeta scintillation counter (Fisher Scientific), respectively. For confocal microscopy, a ScanArray 4000 Microarray Analysis System (Packard BioChip Technologies), including ScanArray Acquisition Software, was used to scan the slides and analyze data, respectively.

Effect of solution on TSM Response. The TSM sensor devices were placed in the cell holder and connected to the network analyzer. A constant flow of buffer was maintained until a stable frequency was established. At this point, the buffer was changed or 500 μL of various concentrations of avidin or neutravidin were injected. The series resonance frequency was monitored until a new stable frequency value was achieved. The original buffer was then reapplied.

Radiochemical Analysis of TAR-$Tat_{12}$ Interaction. The Tris buffer was initially washed through the flow cell at a flow rate of 0.1 ml/min for 20 min. A 500 μL injection of 1 mg/mL neutravidin was made, followed by additional washing by buffer flow for 30 min. At this point, either 500 μL containing 1 nmol $^{32}$P-labelled $Tat_{12}$ ($Tat_{12}$*) or 500 μL containing 100 pmol $^{125}$I-labelled or cold biotinylated-TAR (B-TAR* or B-TAR, respectively), was injected. For the injection of either $Tat_{12}$* or B-TAR*, the TSM sensor was subsequently washed with buffer for 40 min and then removed from the cell holder and measured. The injection of B-TAR was followed with 75 min of buffer washing and injection of 500 μL of 1 nmol $Tat_{12}$*. The TSM sensor surface was then washed with continuous flow of buffer for 40 min, removed and measured. For some experiments, this last procedure was repeated.

Network Analysis of Hybridization. The buffer was initially washed through the flow cell at a flow rate of 0.075 mL/min. The flow of the buffer was maintained until a stable frequency reading was attained. A 500 μL volume of a 1 mg/mL solution of neutravidin was then injected. The pump was stopped when the injection was completed for approximately seven minutes before the flow stream was switched back to the buffer. After the frequency was observed to maintain a level reading, a 500 mL aliquot of solution containing biotinylated F1 was injected into the flow system. The pump was then stopped to allow the neutravidin-biotin reaction to equilibrate. The buffer solution was applied after this step. A 500 μL aliquot of non-biotinylated nucleotide was injected subsequent to the observance of a stable frequency. Again, the pump was stopped to allow the interaction between the immobilized oligo and the probe oligo to equilibrate. The buffer was then reapplied to the modified crystal surface. Variations of this basic procedure were performed to study the hybridization events at higher flow rates. A nominal flow rate of 0.3 mL/min was used for these experiments.

Network Analysis of TSM Sensor Regeneration by λ-exonuclease. The experimental protocol was followed as described above with the exception that, following the stabilization of the immobilized biotin-F1, the buffer was switched from Tris buffer to Glycine buffer. All of the reactants used in subsequent steps were also suspended in Glycine buffer. The frequency was monitored and, after re-stabilization, target oligonucleotide was introduced. Once again, the pump was stopped to allow complete interaction of probe and target before reintroducing buffer. Once the frequency was again stable, 80 μL of dilute λ-exonuclease (5 μL λ-exonuclease+75 μL buffer) was introduced, followed immediately with 80 μL of buffer. The pump was then stopped for 15 min before reintroducing constant flow of buffer. At this point, the experiment may be stopped or cycled through the target hybridization and λ-exonuclease digestion steps a number of times.

$^{32}$P Labelling of Nucleic Acids. A solution of 42 to 200 pmol of nucleic acid, T4 Polynucleotide Kinase (PNK), T4 PNK buffer, and [γ-$^{32}$P] ATP was incubated for 15 min at 37° C. The reaction solution was then extracted with d.d. $H_2O$, NaOAc and phenol/chloroform/isoamyl alcohol after centrifuging for 15 min following vigorous mixing. The aqueous layer was washed with chloroform to remove traces of phenol. Three volume equivalents of ethanol were added to the aqueous layer and this solution was kept on dry ice 30 min to overnight. The supernatant was drawn off subsequent to centrifugation for 30 min. The nucleic acid pellet was washed with ethanol and centrifuged for 15 min, again drawing off the supernatant and allowing the pellet to dry.

Radiochemical Analysis of Hybridization and Regeneration. These experiments were performed without the use of the network analyzer and, thus, the frequency was not monitored for stabilization prior to carrying out each step. Hence, each step of the protocol was performed according to a predetermined time outline as shown in Table 1.

TABLE 1

Radiochemical Analysis of Hybridization and Regeneration

| Time (min) | A | B | C | D | E |
|---|---|---|---|---|---|
| 0 | Tris buffer | Tris buffer | Tris buffer | Tris buffer | Tris buffer |
| 60 | neutravidin | neutravidin | neutravidin | neutravidin | neutravidin |
| 90 | Gly buffer | biotin-F1 | biotin-F1 | biotin-F1 | biotin-F1 |
| 105 | 5'-$^{32}$P-F2 | Gly buffer | Gly buffer | Gly buffer | Gly buffer |
| 120 |  | 5'-$^{32}$P-F2 | 5'-$^{32}$P-F2 | 5'-P-F2 | 5'-P-F2 |
| 135 | STOP |  | λ-exo/stop | λ-exo/stop | 5'-$^{32}$P-F2 |
| 150 |  | STOP |  |  |  |
| 165 |  |  |  |  | STOP |
| 225 |  |  | start pump | start pump |  |
| 285 |  |  | STOP | 5'-$^{32}$P-F2 |  |
| 315 |  |  |  | STOP |  |

As outlined above, the TSM sensor was exposed to λ-exonuclease for 90 min instead of 15 min, as in the network analyzer experiments. An additional series of experiments was performed reducing the exposure time back to 15 min, for comparison. All cpm values were corrected for background cpm by subtracting the counts obtained from pure scintillant. Additionally, all counts were corrected to time=0 for each series. The amount of $^{32}$P-F2 was calculated using cpm values obtained from known aliquots of stock diluted by the same volume of scintillant used for each sample.

Fluorophore Labelling of nucleic Acids. The F2 and MN-F2 oligonucleotides were 3'-end labelled with Alexa 546 and non-biotinylated F1 was 3'-end labelled with either fluorescein or BODIPY 630. Approximately 100 pmol of oligonucleotide was incubated with NE Reaction buffer (potassium acetate, Tris acetate, magnesium acetate, DTT), $CoCl_2$, Alexa 546 dUTP, d.d. $H_2O$, and deoxynucleotidyl transferase for 15 min at 37° C. Subsequent to incubation, the reaction solution was mixed and then incubated for 10 min at 70° C. Purification of the labelled oligos was achieved using the Centri-Sep columns and accompanying protocol.

Preparation and Silanization of Glass Substrate. The glass slides were cleaned by immersion in 25% aqueous ammonia solution overnight and then rinsing with d.d. $H_2O$ for 10 min followed by anhydrous EtOH. The clean slides were then immersed in a 1% 3-mercaptopropyl trimethoxysilane (MPTS), 95% EtOH, and 16 mM acetic acid solution for 30 min at room temperature. This was followed by rinsing with 95% EtOH/16 mM acetic acid (pH 4.5) and then curing under nitrogen for two hours. The slides were stored in a dessicator until required.

Immobilization of Modified Oligonucleotides onto Silanized Glass. The oligonucleotide was diluted with 500 mM NaHCO$_3$/NaH$_2$CO$_3$ buffer (pH 9.0) to a concentration of 10 µM and spotted onto the silanized glass slide surface. The slides were incubated in a humid chamber for two hours at room temperature. The immobilized slides were then washed with TNTw solution (10 mM Tris-HCl, pH 7.5, 150 mM NaCl, and 0.05% Tween 20).

Confocal Microscopy Analysis of Hybridization and Regeneration. The slides were placed in humid chambers for five minutes to hydrate them. The labelled target ($\geq$1 µM) was deposited onto the probe-modified areas using a dropper or the arrayer, under dark conditions. The humid chamber was then sealed and incubated for one hour at 37° C. The slides were then briefly rinsed with a 1 M Tris-HCl/5 M NaCl solution, followed by curing under nitrogen for 10 min and then rinsing with d.d. H$_2$O. The slides were then scanned using the confocal microscope. To study the regeneration of the probe-modified surface by λ-exonuclease digestion, the slides were first rinsed with the glycine buffer and then dried under nitrogen and then placed in the humid chambers for five min at 37° C. A volume of dilute λ-exonuclease (45 µL+15 µL Gly buffer) was deposited onto the slide over the hybridized area. The chamber was sealed and incubated at 37° C. for 30 min. Following incubation, the slides were rinsed with glycine buffer, dried under nitrogen and scanned. The slides could then be cycled through the hybridization and digestion protocols again.

Example 1

A first oligonucleotide F1 to serve as the probe strand, and a second oligonucleotide F2 complementary thereto, to serve as the test strand, of the following sequences, were synthesized, on an Applied Biosystems 392 DNA/RNA Synthesizer, and purified with cartridges and protocol purchased from Applied Biosystems, Mississauga, ON, Canada:

```
F1:
5'-biotin-TATAAAAAGAGAGAGAGATCGAGTC-3'   SEQ ID NO:1

F2:
5'-GACTCGATCTGTCTCTCTTTTTATA-3'          SEQ ID NO:2
```

Oligonucleotide probes having the sequence F1 according to SEQ ID No. 1 were immobilized by bonding, via the 5' end, to the surface of piezoelectric, optically polished, 9 MHz AT cut quartz crystals, with gold electrodes (International Crystal Manufacturing, Oklahoma City, Okla., USA). The crystals were treated with neutravidin (ImmunePure™ neutravidin, used as received, from Chromatographic Specialities, Brockville, Ont., Canada, 500 µL volume of a 1 mg/mL solution). The quartz crystal assembly was mounted in a flow cell of the type described in Canadian Patent Application No. 2,271,179 to Sensor Chem International Corporation (published Nov. 5, 2000). The oligonucleotide was bonded chemically to the neutravidin on the crystal surface via the biotin moiety, by feeding a 500 µL aliquot of a solution containing biotinylated F1 in Tris buffer (10 mM Tris, from Life Technologies, Burlington, Ont., Canada; 70 mM NaCl; and 0.2 mM EDTA from Sigma-Aldrich).

Oligonucleotide F2, according to SEQ ID NO:2, was dissolved in the same Tris buffer and was flowed across the surface of the crystals carrying immobilized F1. Hybridization of the target oligonucleotide F2 to the probe oligonucleotide F1 was determined acoustically, from changes in piezoelectric characteristics of the quartz crystal, as described in Canadian Patent Application No. 2,271,179.

After thorough washing with Tris buffer, the crystal surface carrying the immobilized, hybridized oligonucleotide was treated in the flow cell with 80 µL of dilute λ-exonuclease (Life Technologies, Burlington, ON, Canada, used as received), at 37° C., followed by 80 µL of buffer. Flow was stopped after 15 minutes. Acoustic analysis conducted following the enzyme reaction indicated that the F1/F2 complex had de-hydridized, and that oligonucleotide probe F1 remained bound to the quartz crystal surface, ready for re-use in a further hybridization experiment.

Example 2

A fluorophore-labelled oligonucleotide probe is covalently attached at the 5' end to a silanized glass slides via a disulfide linkage. The slide is subjected to hybridization with a labelled nucleic acid target strand radiochemically labelled with $^{32}$P. Once hybridizaion has occurred, it is confirmed by isotopic measurements. The microarray is then treated with λ-exonuclease to allow digestion of the hybridized probe-target duplex. The slide is washed and confirmation that the microarray has been regenerated is evaluated using $^{32}$P evaluation of the microarray.

Example 3

Avidin is used widely in bioanalytical chemistry in order to immobilize biological species, such as nucleic acids, to substrates, through the strong bond it forms with the biotin moiety. It is common practice to synthesize DNA and RNA molecules with biotin placed at the 3' or 5' end of the nucleic acid chain. Avidin is a basic, homotetrameric glycoprotein having a total molecular mass of 67–68 kDa. The protein possesses a disulfide bond in each subunit and is expected to be adsorbed readily onto gold via a metal-sulfur interaction. Each subunit is capable of binding a biotin moiety with an affinity of $10^{15}$ M$^{-1}$. Neutravidin does not contain a carbohydrate residue, has a molecular weight of 60 kDa and binds biotinylated species with approximately the same affinity as the parent avidin molecule.

Figure 2:
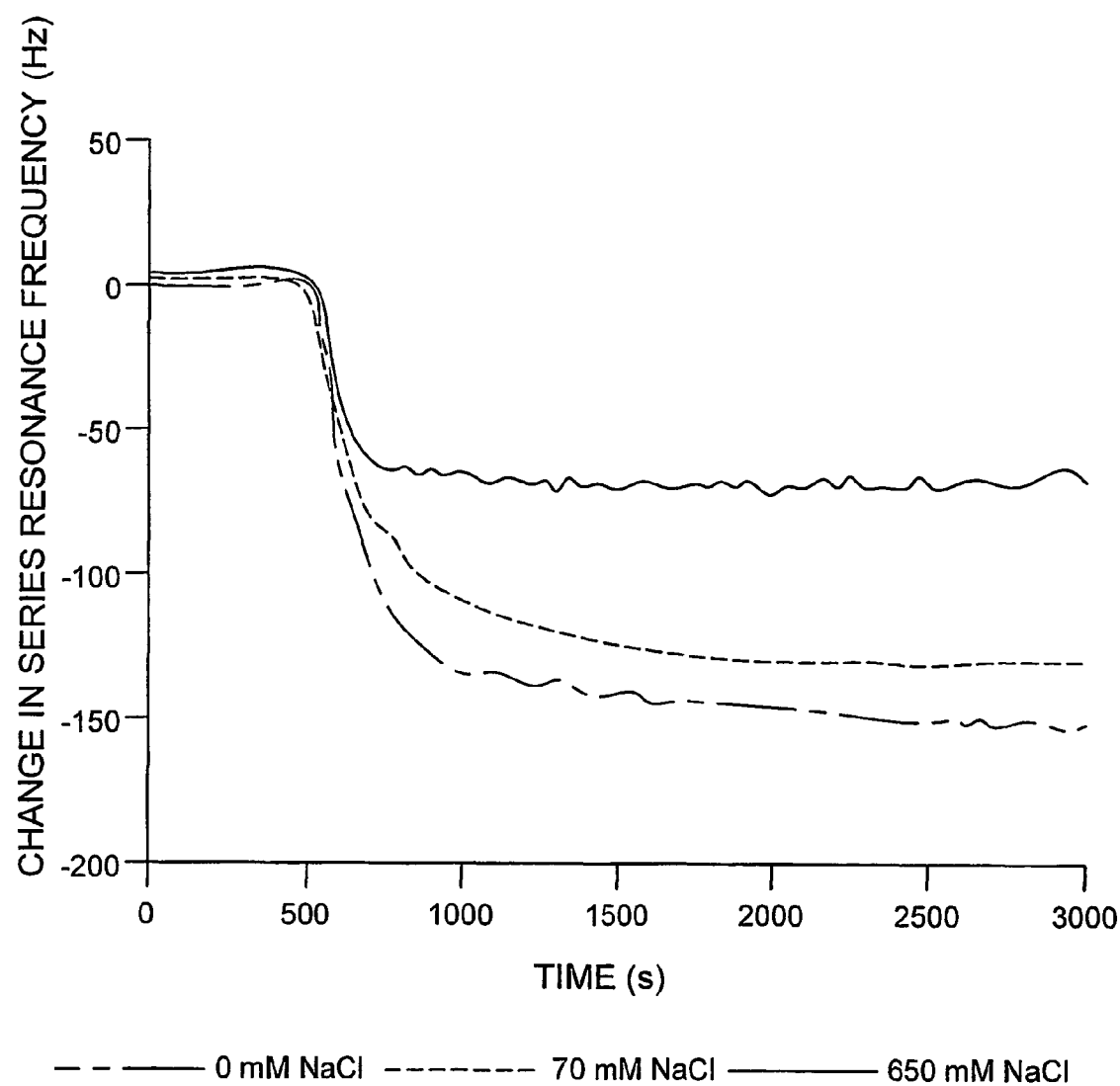
FIG. 2 illustrates the response of a 9 MHz TSM sensor with a rough gold electrode to avidin (10 mg/ml) in various concentrations of electrolyte. NaCl concentrations of 0, 70, and 650 mM are shown.

Effect of Buffer on Avidin Adsorption. In order to ascertain the optimum conditions for the real-time measurement of biotinylated RNA-peptide interactions (next section) the flow-injection analysis (FIA) adsorption of avidin and neutravidin to the TSM surface was assessed. FIGS. 1 and 2 depict the responses of plasma-cleaned gold surfaces to the introduction of avidin solutions containing buffer with different electrolyte concentrations and for electrodes displaying two different morphologies.

FIG. 1 shows the response of a 9 MHz TSM sensor with a polished gold electrode to avidin (10 mg/ml) in various concentrations of electrolyte. NaCl concentrations of 0, 70 and 650 mM are shown. FIG. 1 shows the series resonance as a function of time for the polished gold-coated quartz crystal when a 10 mg/mL avidin solution of various electrolyte concentrations is flowed over the surface of the sensor. Avidin adsorbed with the highest shift in series resonance frequency when the buffer had a salt concentration of 0 mM or 70 mM NaCl using the polished surface. The shifts in $f_s$ were similar for both at approximately −120 Hz. A buffer having 650 mM NaCl resulted in a much lower shift in $f_s$ of only −60 Hz.

FIG. 2 shows the response of a 9 MHz TSM sensor with a rough gold electrode to avidin adsorption (10 mg/ml) in various concentrations of electrolyte. NaCl concentrations of 0, 70 and 650 mM are provided. The comparative TSM responses using rough, gold-electrode crystals are depicted in FIG. 2. Using the rough surfaces, the results produced were similar with a minor difference in that the 70 mM NaCl buffer produced a slightly smaller shift than the 0 mM NaCl. The observed frequency shifts were −130 Hz and −150 Hz, respectively. The shift in $f_s$ for the 650 mM NaCl buffer for the rough surface was −70 Hz.

Both polished and rough surfaces produce similar trends: as the concentration of NaCl is increased from 0 to 70 mM, there is not much difference, however, as it is increased to 650 mM, the shift is significantly diminished. It was observed that, regardless of the surface morphology, a concentration of 650 mM NaCl appeared to interfere with the adsorption of avidin. The results of these experiments confirm that 70 mM NaCl represents an optimum electrolyte medium both in terms of the level of electrode-protein interaction and macromolecular stability. Surface blocking by adsorption of electrolyte and/or ionic strength changes resulting in protein structural change may by responsible for the diminished response to protein at the high concentration of electrolyte, and for the reversal of behaviour at the 0 and 70 mM values for the two surfaces. There is marginal increase in protein adsorption for both sets of experiments when a rough electrode morphology is employed; this is clearly connected to the compromise between increased electrode surface area and the ability of the protein to form a packed layer on the surface.

To further study the adsorption of avidin, detergent was added to the buffer used to make up the avidin solution. It was observed that the addition of detergent did not yield an increase in the series resonance frequency for the adsorption of avidin. It might be expected that the time required to reach maximum frequency would decrease due to the fact that detergents are generally used to denature proteins. This was not observed. The denaturing of the quaternary structure would result in the increase of molecules passing over the surface. For example, if the bonds between the subunits were disrupted, there would be four times as many molecules in the solution as original avidin molecules. This would increase the probability of the surface interacting with one of them. In addition, the subunits would become bulkier with a loss of tertiary structure. This expansion of the surface area of the proteins would increase the probability of interactions at the surface of the crystal.

Figure 3:
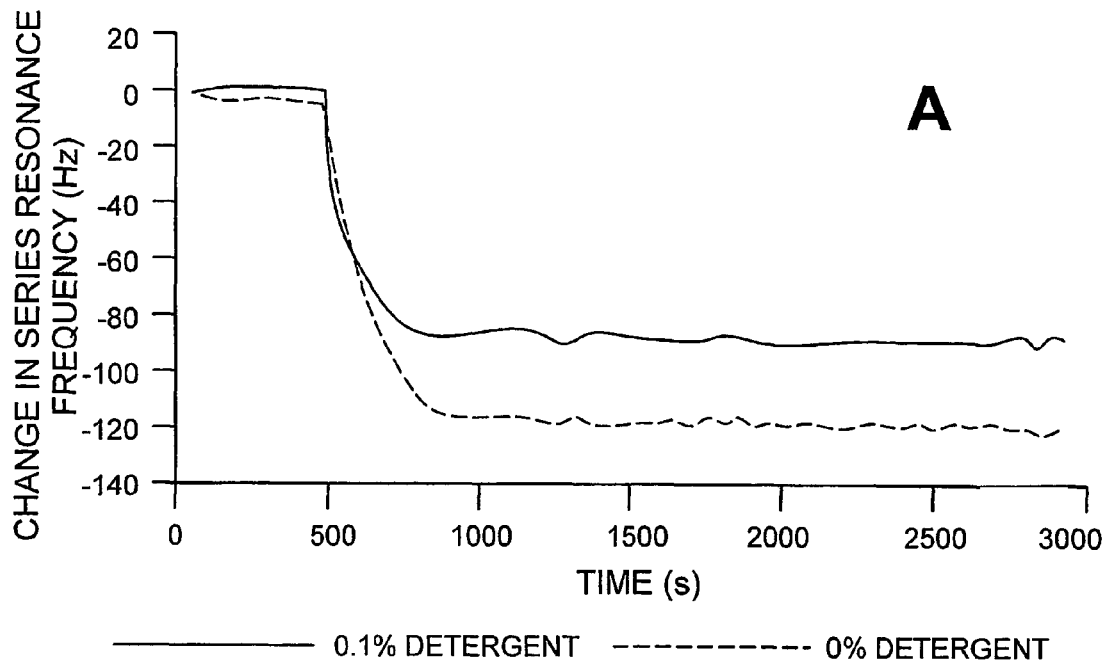
FIG. 3 shows series resonance frequency response for adsorption of 10 μg/ml avidin in 0% and in 0.1% detergent solution on (a) polished and (b) rough, 9 MHz, gold-electrode TSM devices.
Figure 3:
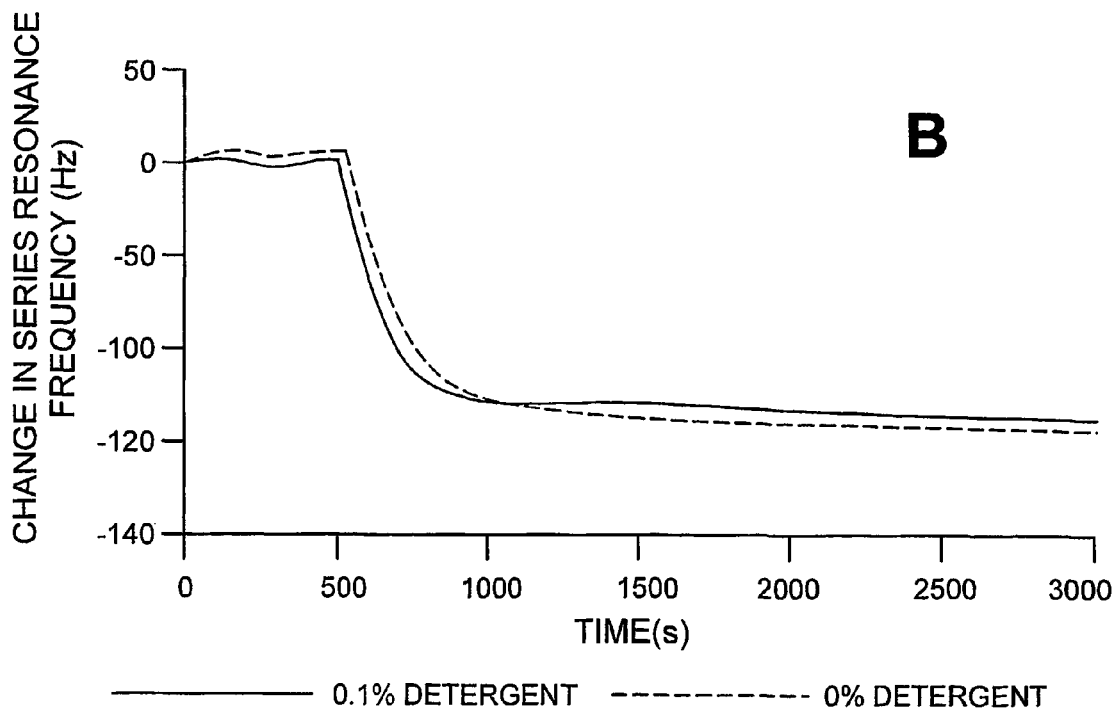

FIG. 3 illustrates the series resonance frequency response for adsorption of 10 μg/ml avidin in 0% and in 0.1% detergent solution on (a) polished and (b) rough 9 MHz gold-electrode TSM devices. As the protein is further denatured, it would be expected that the time required to reach maximum adsorption would decrease due to the subsequent increases in both surface area and number of molecules. As well, the change in series resonance frequency would decrease because the resultant molecules would have lower molecular mass than native avidin. However, denaturation would also affect the disulfide bond of the avidin subunits. This would decrease the adsorption of protein, as this characteristic of secondary structure is essential to surface interaction. Using the rough gold crystals, the frequency shifts were the same for both the experiment using the original buffer and the experiment using the buffer containing 0.1% (w/v) of the detergent to make up the 10 μg/mL avidin solution. As shown in FIG. 3(a), polished crystals resulted in an approximate frequency shift of −150 Hz. The results were slightly different using the smooth crystals as shown in FIG. 3(b). The frequency shifts for the runs using the original buffer and the 0.1% detergent buffer were −120 Hz and −90 Hz, respectively.

Figure 4:
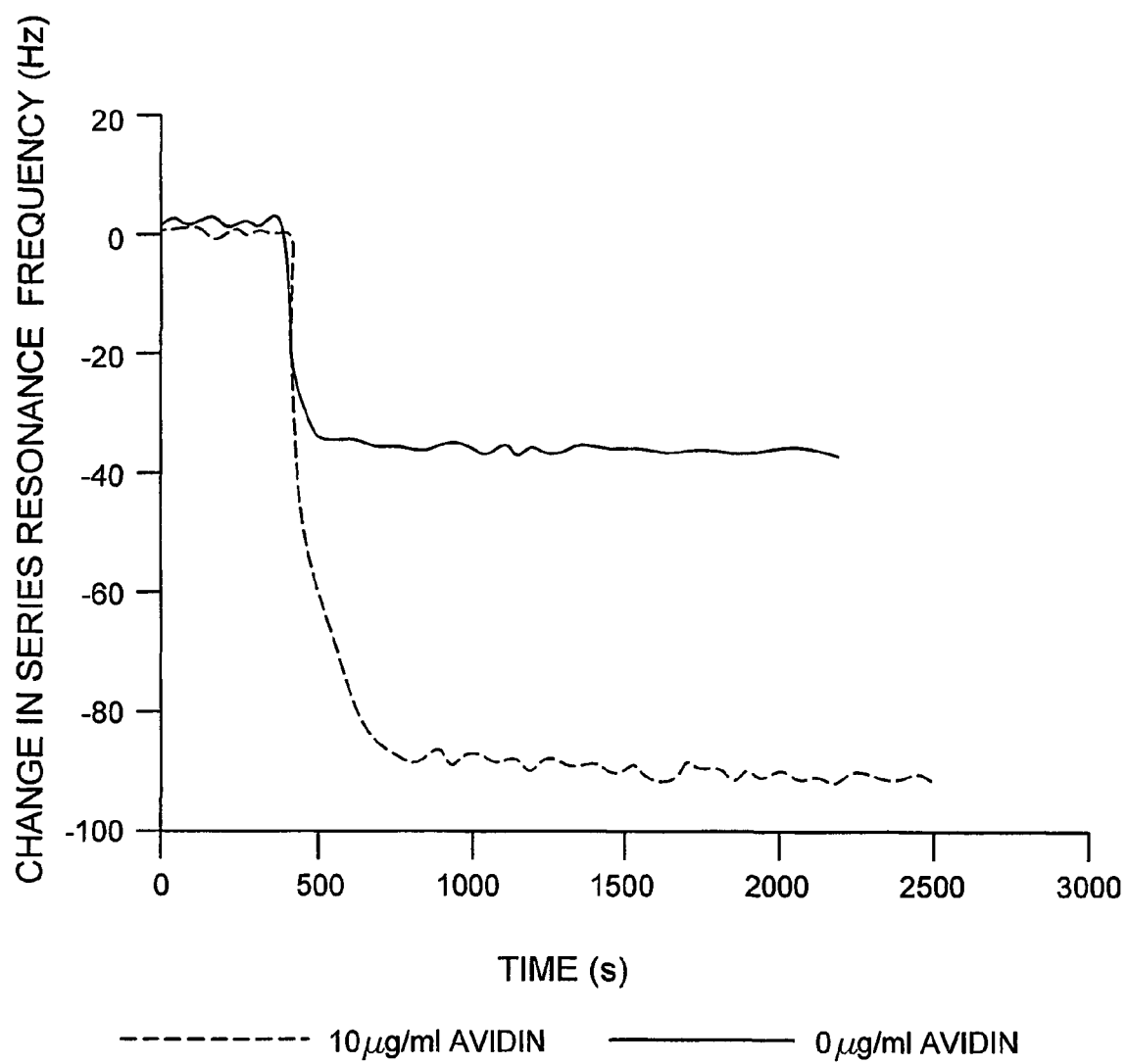
FIG. 4 shows a comparison of absolute changes in frequency for 10 μg/ml avidin in 0.1% detergent solution and for 0.1% detergent solution alone.

FIG. 4 shows a comparison of frequency shifts for the injection of the detergent-containing buffer without avidin and the injection of the 0.1% detergent buffer with an avidin concentration of 10 μg/mL showed that the detergent adhered to the surface. A frequency shift of −34 Hz was observed for the injection of the buffer without avidin and −90 Hz for the buffer with avidin.

Figure 5:
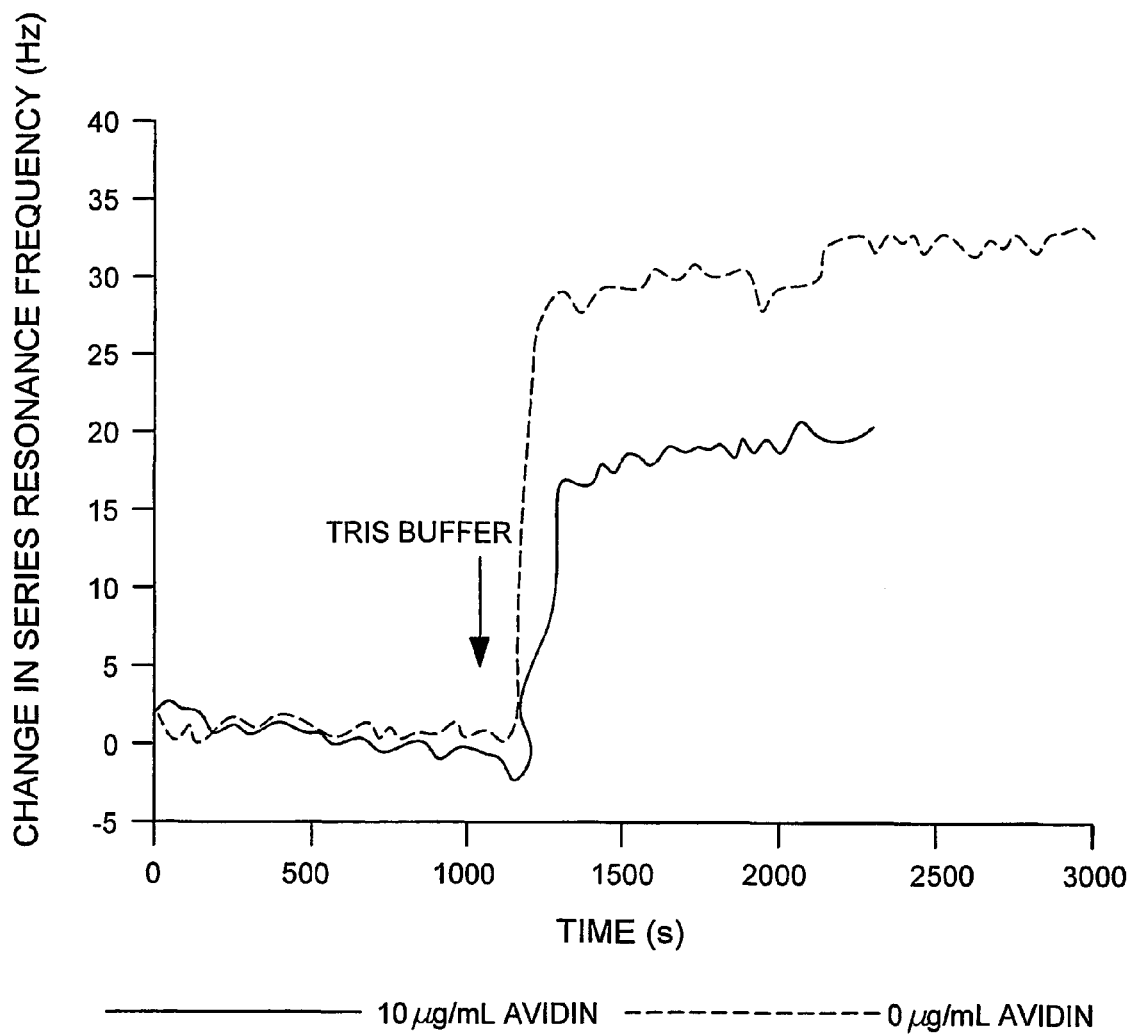
FIG. 5 is a comparison of frequency responses for reintroduction of Tris buffer following treatment with μg/ml avidin in 0.1% detergent and with 0.1% detergent alone.

However, upon re-application of the original buffer to the treated surface, a frequency increase of 20 to 30 Hz was observed for both cases, as illustrated in FIG. 5 by comparison of frequency responses for reintroduction of Tris buffer following treatment with 10 μg/ml avidin in 0.1% detergent and with 0.1% detergent alone. Since the detergent does not assist in protein adsorption, it is not advantageous to include it in the buffer. In addition, the detergent denatures the avidin and the change in frequency may be the result of ineffective adsorption of the denatured protein.

The Effect of Surface Morphology oil Avidin Adsorption. A comparison of surfaces was performed using gold (polished and rough) and silver (polished) crystal surfaces. The kinetics of adsorption proved to be similar for all three types of crystals. Comparison of the concentration profiles for two of three surfaces—rough gold and polished silver—indicates that that the amount of time required to reach maximum adsorption is the same regardless of the electrode metal and surface morphology. The shifts on the rough Au crystal surface ranged from −100 Hz to −155 Hz and on the polished Ag surface from −95 Hz to −155 Hz. The shift observed for 10 μg/mL avidin injection with the polished Au surface was at the midpoint of this range at a value of −120 Hz.

Adsorption of Neutravidin. Neutravidin can be substituted for avidin, as a substrate for biotin. For concentrations of neutravidin greater than 5 μg/mL, maximum adsorption is reached after approximately 1000 s. However, the equivalent adsorption of neutravidin requires an increasingly longer period of time with decreasing concentrations. Although a minor disadvantage when it comes to real-time measurements with biotinylated species, neutravidin yields a significantly larger frequency shift which, in part, may be associated with a higher packing density of the electrode surface. Moreover, hydrophilic adsorptive surfaces appear to compromise the integrity of the biotin binding sites in the parent molecule. This is likely caused by reorientation phenomena related to polar surface-carbohydrate interactions.

Surface Characterization. To characterize the polished crystals that were subjected to a plasma cleaner and those that were not, stationary contact angle measurements were obtained from both types of surfaces. The crystals that were not plasma cleaned were found to have an average contact angle of 80° with a standard deviation of ±5°. The crystals subjected to plasma cleaning and directly measured were found to have an average contact angle of 47° with a standard deviation of ±6°. Crystals that were subjected to plasma cleaning and kept in a closed container for 12 days were found to have a contact angle of 50° with a standard deviation of ±12°. These results prove that the cleaning treatment significantly alters the surface free energy of the crystal surface. The crystals that were plasma cleaned were hydrophilic relative to the crystals that were not. This alteration of the surface free energy was also shown to persist over at least a number of days by the observance that the crystals retained their hydrophilic character after almost two weeks. The higher standard deviation, however, may indicate that the surface changes over time. The high standard deviations with all three surface types may be attributed to the fact that the crystals are unique; they are all manufactured according to the same process, yet no two crystals can be guaranteed to have the same surface properties. Due to differentiation in surfaces, each will respond uniquely to treatment by plasma cleaning.

Further characterization of the hydrophobic and hydrophilic surfaces was carried out by X-ray photoelectron spectroscopy (MS). Spectra were obtained for both surface types under the conditions of adsorbed avidin, adsorbed neutravidin and no protein adsorption. Protein adsorption was achieved by the methods previously described, up to and including the second buffer wash. This wash was included in order to eliminate any loosely bound protein from the surface that would normally be washed from the surface at this point in a general run. Thus, XPS was performed on the surface that the biotinylated TAR RNA would encounter. Elemental analysis was executed for oxygen, carbon, and gold on the bare surfaces and nitrogen was added to the list of elements for the protein-adsorbed surfaces. The addition of nitrogen analysis was included for the protein-treated surfaces because proteins have peptide bonds and this analysis would give a verification of the presence of protein on the surface. Additionally, there was no noticeable peak for nitrogen in the survey plots for the bare surfaces to justify high resolution analysis of the nitrogen peak range for these surfaces. The results are tabulated in Table 2, showing surface elemental composition data collected from XPS analysis of protein-adsorbed and bare 9 MHz, polished, gold-electrode TSM devices which have undergone plasma-cleaning (hydrophilic) and non-plasma-cleaning (hydrophobic) procedures. From the percent atomic composition given, it was observed that there were significant differences in the C:O ratios of the hydrophilic and hydrophobic surfaces for both the avidin-treated and bare surfaces.

TABLE 2

Surface elemental composition data from XPS analysis of protein-adsorbed and bare TSM devices after hydrophilic and hydrophobic procedures

| Protein | Surface | % C | % N | % O | % Au |
|---------|---------|-----|-----|-----|------|
| none | hydrophobic | 44 | | 2 | 54 |
| none | hydrophilic | 31 | | 9 | 60 |
| avidin | hydrophobic | 60 | 5 | 19 | 16 |
| avidin | hydrophilic | 44 | 9 | 25 | 22 |
| neutravidin | hydrophobic | 58 | 7 | 24 | 11 |
| neutravidin | hydrophilic | 57 | 9 | 26 | 8 |

The implication is that the plasma cleaning treatment interacts with hydrocarbon impurities on the surface to force this alteration in relative atomic composition. This, in turn, affects the interaction of avidin with the gold surfaces. The high resolution spectra of the C1s and O1s regions show significant differences between the hydrophilic and hydrophobic surfaces for both conditions. The C1s spectrum of the hydrophilic, bare crystal shows a smaller peak for C—C and C—H bonds than the corresponding spectrum for the hydrophobic surface. In addition, there is the appearance of a third peak in the O1s range, which indicates the presence of a highly oxidized oxygen species.

A comparison of the oxygen peaks on the spectra for the avidin-treated surfaces clearly indicates that there is different behaviour of avidin on the two surfaces. On the hydrophobic surface, there is evidence of only one peak, whereas, there is a distinctive second peak at 532 eV for the avidin-treated hydrophilic surface. Furthermore, there is a difference in the spectra for C1s of avidin on the two surfaces. There is a higher content of carboxylic carbon in the spectra for avidin on the hydrophilic surface than on the hydrophobic surface. These differences may be accounted for by the hydrophilic surface inducing a conformational change in the adsorbed avidin. This change may result in the exposure of internal acidic residues to the exterior of the protein. This would explain the increase in the carboxylic carbon peak of the spectrum for avidin on the hydrophilic surface because the XPS analysis depth is only ~50 Å.

Avidin is much greater than 50 Å in diameter and, therefore residues on the interior of the protein would not be detected by XPS analysis. XPS is a dry technique and the conformation of the protein may be compromised from its state in solution. However, both surfaces are studied under the same conditions, varying only in surface hydrophobicity. Hence, the alteration of the protein between liquid and air states may be eliminated as factoring into the difference observed between avidin on the two surfaces. The C1s and O1s spectra for neutravidin adsorbed on the hydrophilic and hydrophobic surfaces do not display any significant differences. Neutravidin appears to interact equally well with both surfaces. This contrast between neutravidin and avidin interactions at the two surfaces may be linked to the fact that avidin has variable carbohydrate prosthetic groups which also interact with the surface and other avidin molecules, whereas, neutravidin does not. These sugar residues may destabilize the avidin molecule when it is attached to a hydrophilic surface to the point that the protein is structurally compromised. This would further explain the observation that the subsequent reactions of B-TAR RNA and $Tat_{12}$ are affected by a hydrophilic surface. If avidin is structurally compromised, the biotin-binding site(s) may be affected and, thus, the TAR RNA would not be properly immobilized on the surface for interaction with $Tat_{12}$.

DNA/DNA Interactions. In the development of a nucleic acid biosensor microarray, it is important to consider the possibility of being able to differentiate various nucleic acid interactions. These include complementary, non-complementary and single-base mismatch interactions, as well as other degrees of non-complementary interactions, such as between single-base and fully non-complementary. Thus, research was performed using a series of synthesized oligonucleotides to study the responses of the TSM acoustic wave device to interfacial hybridization of complementary, non-complementary and single-base mismatch sequences.

Figure 6:
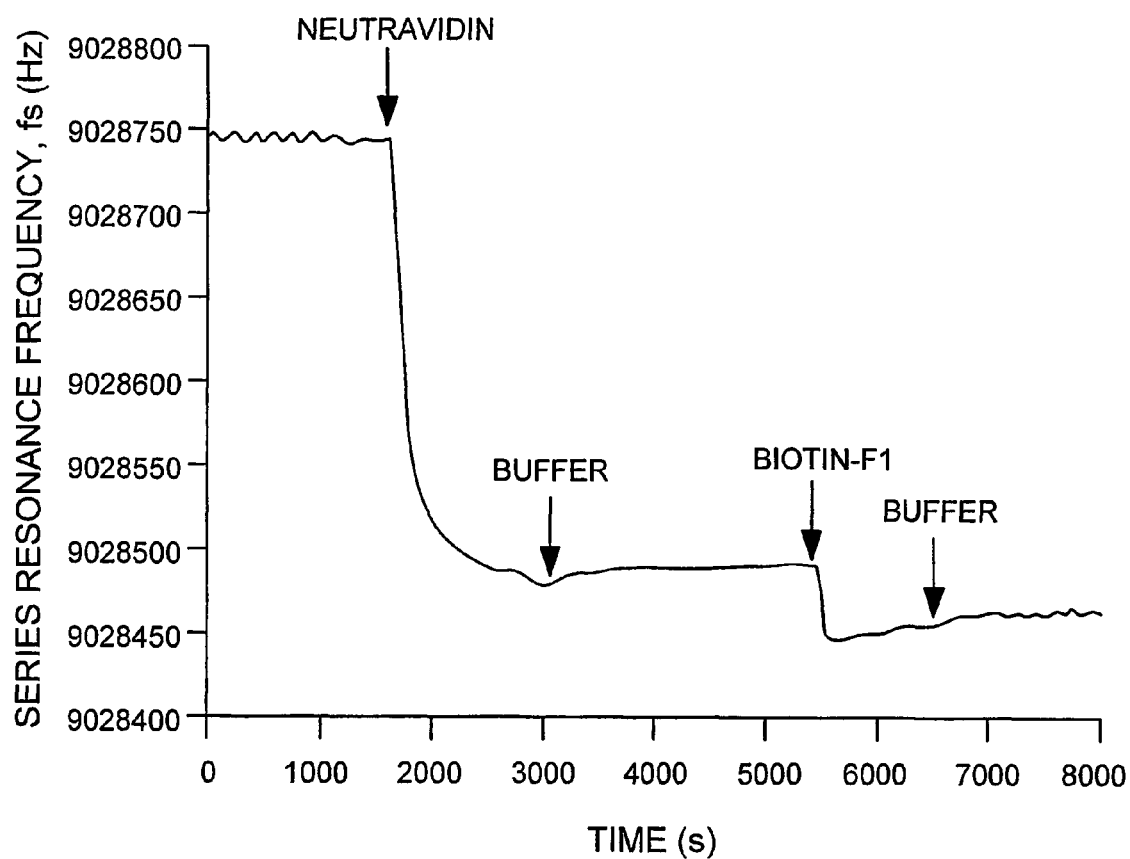
FIG. 6 is a series resonance frequency-time plot for the on-line introduction of neutravidin and biotinylated 25-mer oligonucleotide (F1).

Complementary and Non-Complementary Oligonucleotides. FIG. 6 shows the series resonance frequency ($f_s$) of a TSM sensor as a function of time during the introduction of neutravidin and then the biotinylated oligonucleotide, F1, to the polished Au-electrode of the device. Arrows represent points of injection of indicated solutions. Experiments were conducted under ambient temperature conditions. The adsorption of the protein on the sensor surface is confirmed by the reduction in $f_s$ by a value of, typically, 300 Hz. The frequency decreases a further 50 Hz on exposure of the immobilized protein to the biotinylated oligonucleotide (F1). In subsequent figures, and discussion of them, the responses for neutravidin and F1 are assumed to have occurred for convenience.

Figure 7:
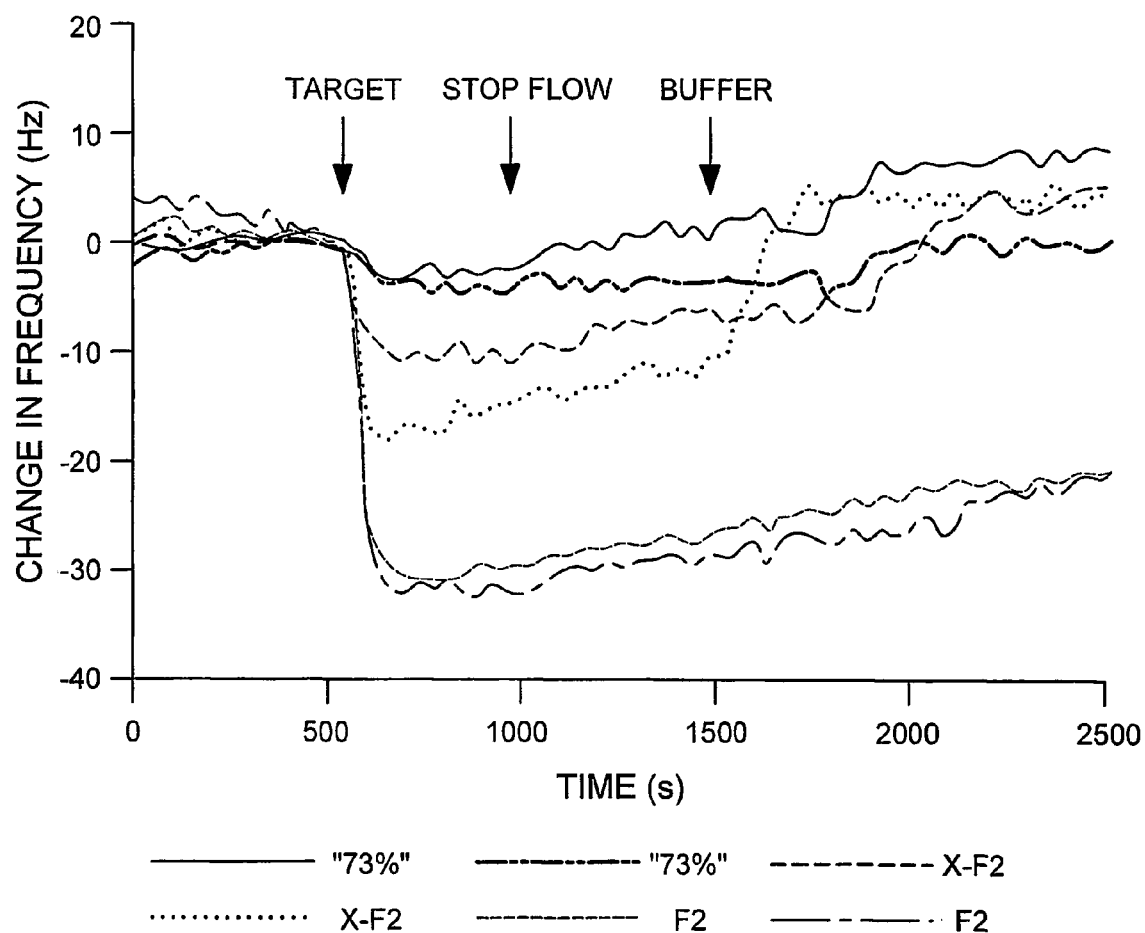
FIG. 7 shows the change in series resonance frequency-time plot for on-line introduction of the complementary oligonucleotide, F2, and non-complementary oligonucleotides, X-F2 and '73%', to surface-attached F1.

FIG. 7 illustrates typical results for experiments involving addition of the complementary (F2) and non-complementary (X-F2 and "73%") oligonucleotides to the system described above. The times of injection of the nucleic acids, the stoppage of flow and reintroduction of buffer are indicated by arrows. Experiments were conducted at ambient temperatures. It is noteworthy that when the surface modified with F1 is challenged with buffer containing the fully complementary sequence there is an initial frequency decrease in the range of 31–42 Hz. This result may be attributable to hybridization of the complementary oligos even under the condition of ambient temperature employed for the experiments. Series resonant frequency versus time plots for experiments in which the modified oligo surface was challenged by the non-complementary strands X-F2 and "73%" show a significant difference from those for complementary strands.

Figure 8:
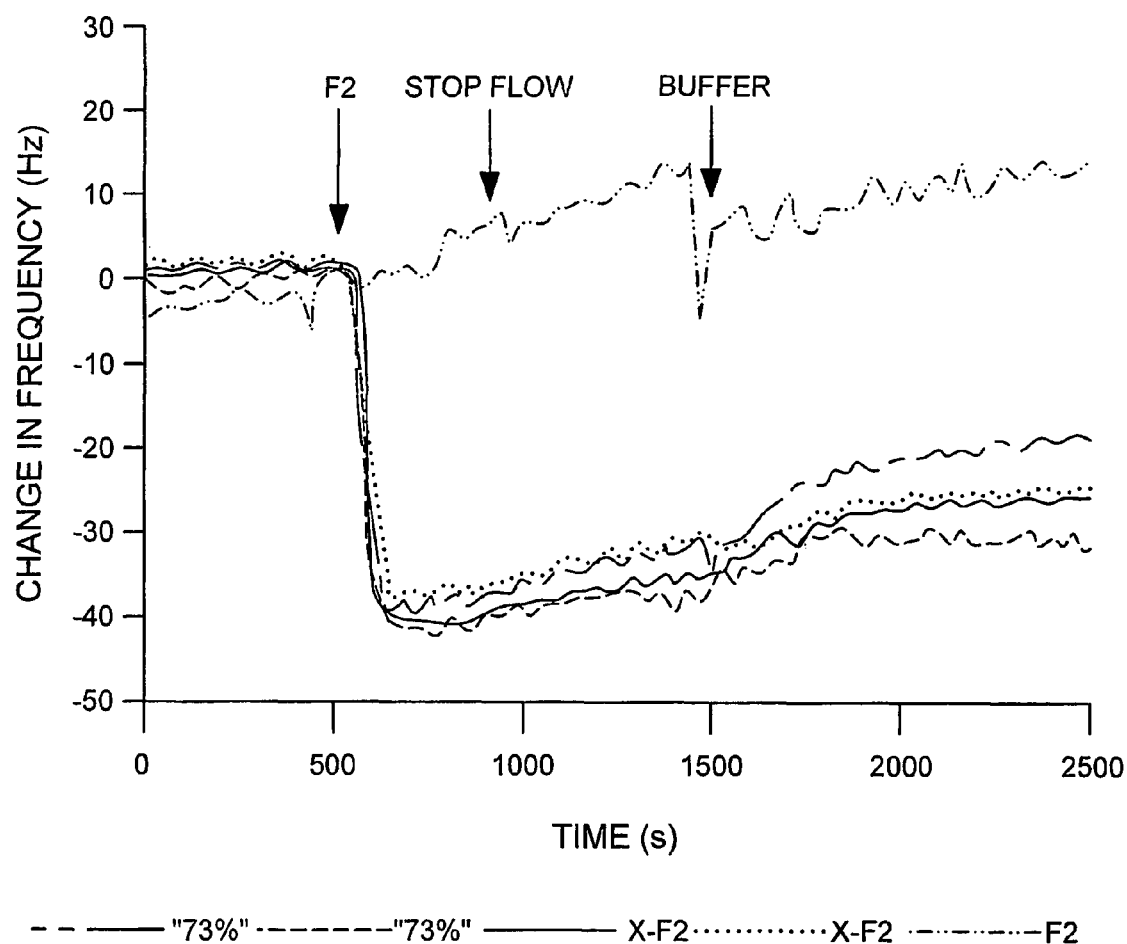
FIG. 8 illustrates is a series resonance frequency time plot for a second challenge of F2 to F1:F2, F1:X-F2 and F1:'73%' systems.

FIG. 8 shows that, the frequency decreases 10 to 15 Hz for the X-F2 oligomers and approximately 5 Hz for the "73%" oligomer followed by stabilization while the crystal surface remained exposed to the DNA-containing solution. Note responses for the latter two cases and no response for the former. The frequency increases to the value observed prior to the injection once the buffer was reapplied to the crystal surface. This may be explained by the formation of intermediates which are subsequently removed by the flow of buffer. The difference in frequency shifts for the interaction of the probe and the oligonucleotides, X-F2 and "73%", can be attributed to the relative percentage of complementarity between these oligomers and F1. The sequence X-F2 has one segment of 11 bases and one of 5 bases that are complementary to F1. In contrast, "73%" has one segment of 4 bases and another of 3 bases that are complementary to F1. Therefore, there is a much higher probability that intermediate hybrids are formed between the probe and X-F2 than between the probe and "73%". In addition, the F1:X-F2 hybrids should be stronger than the F1:"73%" hybrids because potentially more bases are involved in the former.

A particularly interesting feature of the plots depicted in FIG. 7 is the tendency of the value off, to increase for the F1:F2 interaction (on the reintroduction of buffer). Although there is a temptation to attribute this effect to "wash-off" of F2 from the device, in the vein of the mass response dogma, this is not the case as shown by the experiments summarized in FIG. 8. These plots depict further challenges by F2 to both the F1:F2, F1:X-F2 and F1:"73%" systems. Note that in the former case no additional response associated with hybridization occurs implying strongly that no freed F1 sites are available for interaction.

An interesting phenomenon occurred when the flow rate was increased to 0.3 mL min$^{-1}$. The resonant frequency oscillated around the before-injection baseline before settling at a decreased frequency (approximately −30 Hz shift). This may be attributable to the dispersion of the F2 solution into the flow cell and over the surface. Increasing the flow rate increases the pressure in the flow cell and alters the dispersion or concentration profile of the DNA injection relative to the slow flow rate. Thus, it is reasonable that the increased flow rate may induce different hybridization intermediates than those that occur with the slower flow rate.

Figure 9:
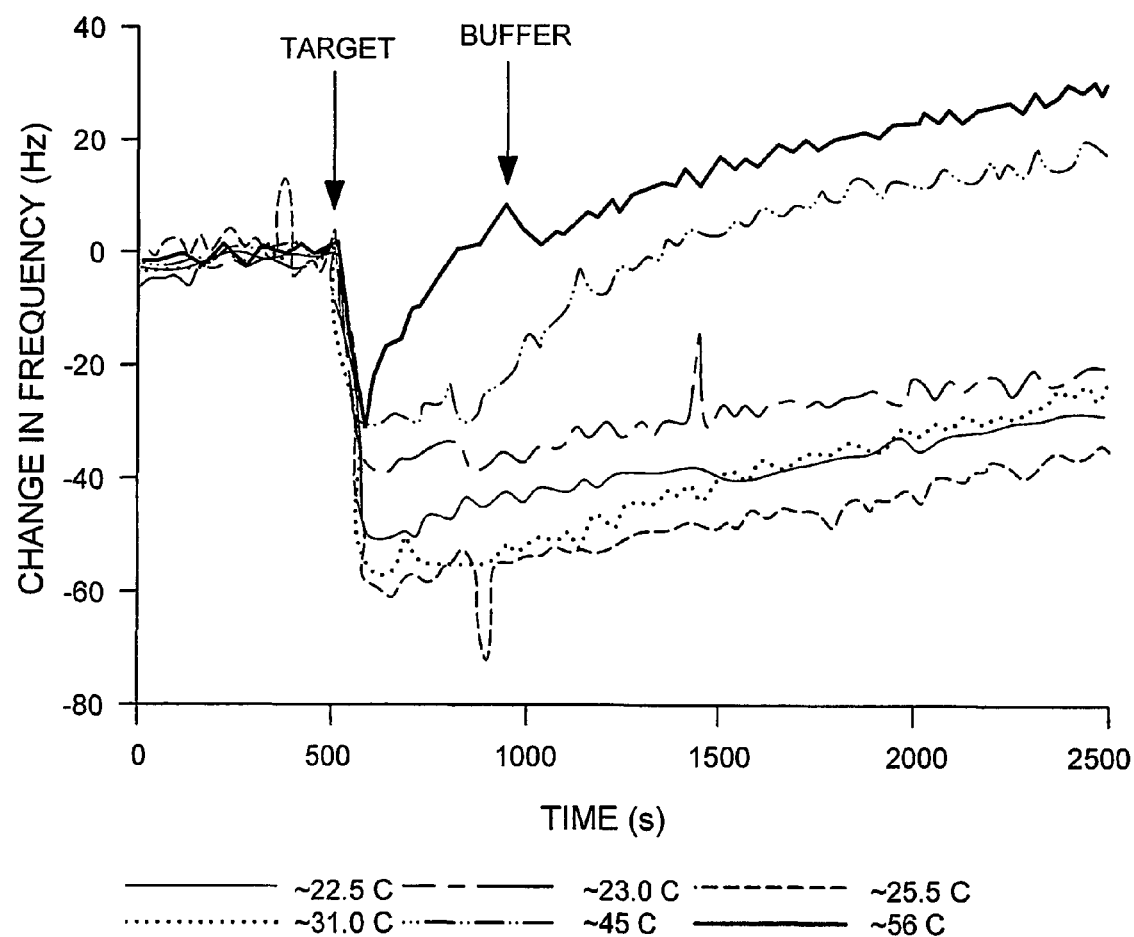
FIG. 9 shows the change in series resonance frequency versus time plot for F1:F2 interaction as a function of temperature.

Complementary Hybridization as a Function of Temperature. Experiments were conducted at various temperatures in a closed, controlled environment (rather than laboratory ambient conditions) to determine the effect of this parameter on the signal associated with the interaction of complementary F2 with probe F1. The results are shown in FIG. 9. At 23° C. a decrease in frequency upon injection of F2 (−38 to −50 Hz) followed by a slow increase was observed, much as described above for the experiments performed under ambient conditions. The results obtained at 25° C. and 31° C. consisted of frequency shifts of −55 and −60 Hz, respectively. However, the reintroduction of buffer resulted in quite different behaviour at these two temperatures in that the return to baseline signal is much more rapid at the higher temperature. We attribute this result to an increased level of annealing of the two strands. At lower temperatures there is a higher probability of the occurrence of incorrect pairing of bases. Experiments conducted at ~45° C. and ~56° C. showed that there was a lower overall change in frequency (~−30 Hz) when the biotinylated probe was challenged with the complementary strand. The series resonance frequency also displayed sharp increases after the injection of the complementary strand; This is probably caused by a combination of the wash-off of the complementary strand and the stability of the formed duplex. The complementary strand does not interact with the same stability at the higher temperatures because these values are very close to the melting temperature of the double strand, 68° C. Accordingly, we propose that the subsequent increase of the signal at these temperatures is due to removal of F2 from the surface and, subsequently, from the cell. This is supported by the fact that at 45° C. the signal resulting from injection of F2 is almost exactly duplicated with a second injection, indicating that the complementary strands present in the second injection are not hindered from interacting with the probe-modified surface. This implies that there is little double-stranded DNA formed to block hybridization. This was not the case at lower temperatures, as discussed above, where it was observed that the first injection of the complementary sequence blocks the subsequent interaction of F2 with F1. Thus, at these temperatures, only unstable hybrids are formed resulting in a rapid decrease of frequency.

The experiments discussed above indicate that the optimum temperature for observing complementary hybridization is in the vicinity of 25° C. However, one of the purposes of the present work is the differentiation of responses for complementary and point mutation sequences and this distinction may be enhanced at a higher temperature. Accordingly, we embarked on a detailed study of the role played by thermal effects for hybridization of F1 with a set of single-base mutated oligonucleotides.

Hybridization with Point Mutated Oligonucleotides. Experiments using the eight DNA sequences synthesized to be one base different from the complementary sequence, F2, were performed under ambient conditions. The results show that these sequences do hybridize with F1. The initial frequency shifts for these point mutation oligomers range from 27 to 38 Hz, which is similar to that observed for hybridization with F2. There appears to be a difference in the general trend observed after the initial frequency shift among these hybridization events and the true hybridization with F2. The frequency of the mutant hybrids tends to drift steadily, approaching the baseline achieved prior to injection, whereas, the F1:F2 hybrids are more apt to drift to a smaller value and then stabilize. However, as with the complementary strand experiments, F2 (not the mutant) is inhibited from attaching to F1. Accordingly, the drift behaviour must reflect different annealing rates with the mutated nucleic acid.

In order to ascertain the effect of hybridization temperature on the ability to distinguish complementary and single-base mutation chemistry, experiments were performed for five of the specified eight sequences (F2-T14A, F2-T4C, F2-T4G, F2-C21A and F2-C21T) at 55 ° C. A sixth sequence, F2-T14C, was studied at 50° C. The greatest change in frequency (~−30 Hz) occurred when F1 was challenged with complementary strand F2. Substitution of a cytidine for and a thymidine at position 14 (F2-T14C) produced a profile at 50° C. similar to that for the fully complementary sequence at 55° C. with the exception that the initial change in frequency was smaller (~−25 Hz).

Comparing this with the results obtained for F2-T14A at 55° C. shows that there is a smaller change in frequency for the substitution of a purine for a pyrimidine than for the substitution of a pyrimidine for another pyrimidine. In addition, the off-rate for F2-T14A appears to be higher than that for F2-T14C. This can be attributed to the difference in temperature at which the two experiments were performed, although, considering the similarity of the responses observed for F2 at these two temperatures, this factor plays a very small role. More likely, the difference lies in the fact that the hydrogen bonding and stacking interactions between the two strands are more perturbed with the T to A mutation than the T to C. This middle sequence is special in that it has purines on one strand and pyrimidines on the other. Substituting a pyrimidine on the purine strand would greatly disrupt the stacking of this purine:pyrimidine sequence, more so than the loss of hydrogen bonding by substituting a pyrimidine for another pyrimidine. If full hybridization interactions occur, the F2-T14A mutant forces two adenosine bases to interact, whereas, the F2-T14C mutant puts a cytosine opposite an adenosine. However, it must be kept in mind that the response for both of these is still within 10 Hz of the response for F2. This suggests that the mutation of a base in the middle of a 25-mer sequence does not alter the hybridization kinetics to a significant extent.

Mutating the base at the 4-position resulted in two very different responses. Substituting thymine for cytosine (F2-T4C) produced a response similar to that observed for F2-T14A. The initial decrease in frequency was 20 Hz followed by a sharp rise in series resonance frequency and stabilization of the signal at about 15 Hz above the baseline established prior to injection of the target.

The observed response for substitution of the thymine for guanosine at this same position was different in that the initial change in series resonant frequency was only about −13 Hz. This observed discrepancy again shows the importance of the stacking stabilization of the double helix. Substituting a pyrimidine for another pyrimidine destabilizes hybridization interaction to a lesser extent than substituting a purine for a pyrimidine. This also points to the importance of end effects, particularly for short oligomers. Disrupting the base-pairing towards the end of the double strand has a greater effect on the overall stability of the hybrid than disrupting base-pairing in the middle as evidenced by the smaller change in initial frequency for the T4 mutants relative to the T14 mutants.

The C21 mutants resulted in series resonance frequency profiles similar to F2-T4G. Substituting cytosine for adenosine or thymine did not produce different initial frequency shifts; both resulted in a decrease of approximately 12 Hz. However, the off-rates were markedly different. The subsequent rise in frequency for F2-C21T was much sharper than for F2-C21A. This may be explained again by the fact that this substitution is a purine for a pyrimidine and would be more disruptive than the pyrimidine-pyrimidine substitution.

Double-stranded oligonucleotides in bulk solution have dynamic zippering and unzippering along about 5 base pairs of the double strand at both ends, a phenomenon called "end effects". Thus, in bulk solution, it would be expected that mismatches at the ends affect the hybridization to a lesser extent than mismatches imposed towards the middle of the strand. This does not appear to be the case for surface-attached oligonucleotides. It is possible that "end effects" only apply to the free end of the ds-oligonucleotide and not the immobilized end. This would explain the observation that the TSM, sensor is more sensitive to substitutions made at the surface end of the target (T4) than to substitutions made at the end of the target positioned away from the surface of the crystal (C21). Because of the end effects, the C21-mismatch targets do not behave much differently than the fully complementary targets. The structure and, hence, the behaviour of the T4-mismatch targets are significantly perturbed relative to the fully complementary targets. Assuming that the same amount of target interacts with the probe surface in each case, the mass deposition is not altered. However, the disruption of the base pairing at the surface would possibly contribute to changes in the viscoelasticity and slip parameters which influence the TSM response.

Regeneration of probes by Lambda-Exonuclease. A nucleic acid biosensor system according to the invention is able to regenerate the original probe surface. A typical TSM cell is made of Plexiglas and, as such, cannot endure the use of solvents. The TSM responds to temperature fluctuations and changes in electrolyte concentration, as well as solution composition. The probe strand is surface-attached (so as to be immobilized) via a protein-substrate interaction and the protein is sensitive to many conventional methods for denaturing dsDNA. Thus, a biosensor system according to the invention includes means for melting or denaturing the double-stranded nucleic acids without using the conventional techniques of temperature and/or solvent manipulation. Proteins are used iii vivo to manipulate DNA for transcription, replication, translation, regulation, repair, etc. Lambda-exonuclease, a commercially available nucleic acid enzyme (nuclease) has this effect. Lambda-exonuclease is a trimeric toroidal protein, which attaches to dsDNA and digests a single strand processively in the 5' to 3' direction, while leaving the opposing strand intact. This is desirable according to this embodiment of the invention because the probe was labelled with a biotin at its 5'-end and would, thus, was unavailable for enzyme attachment. Hence, the target strand was selectively digested and the probe strand remained intact. This enzyme is most active against blunt-ended dsDNA with an available 5' phosphate. Lambda-exonuclease uses $Mg^{2+}$ as a co-factor and, thus, a different buffer (Glycine) was incorporated into the experimental procedure. Experimental data illustrated that it was advantageous to change the buffer system after the attachment of the biotinylated probe and subsequent washing with the Tris buffer.

Figure 10:
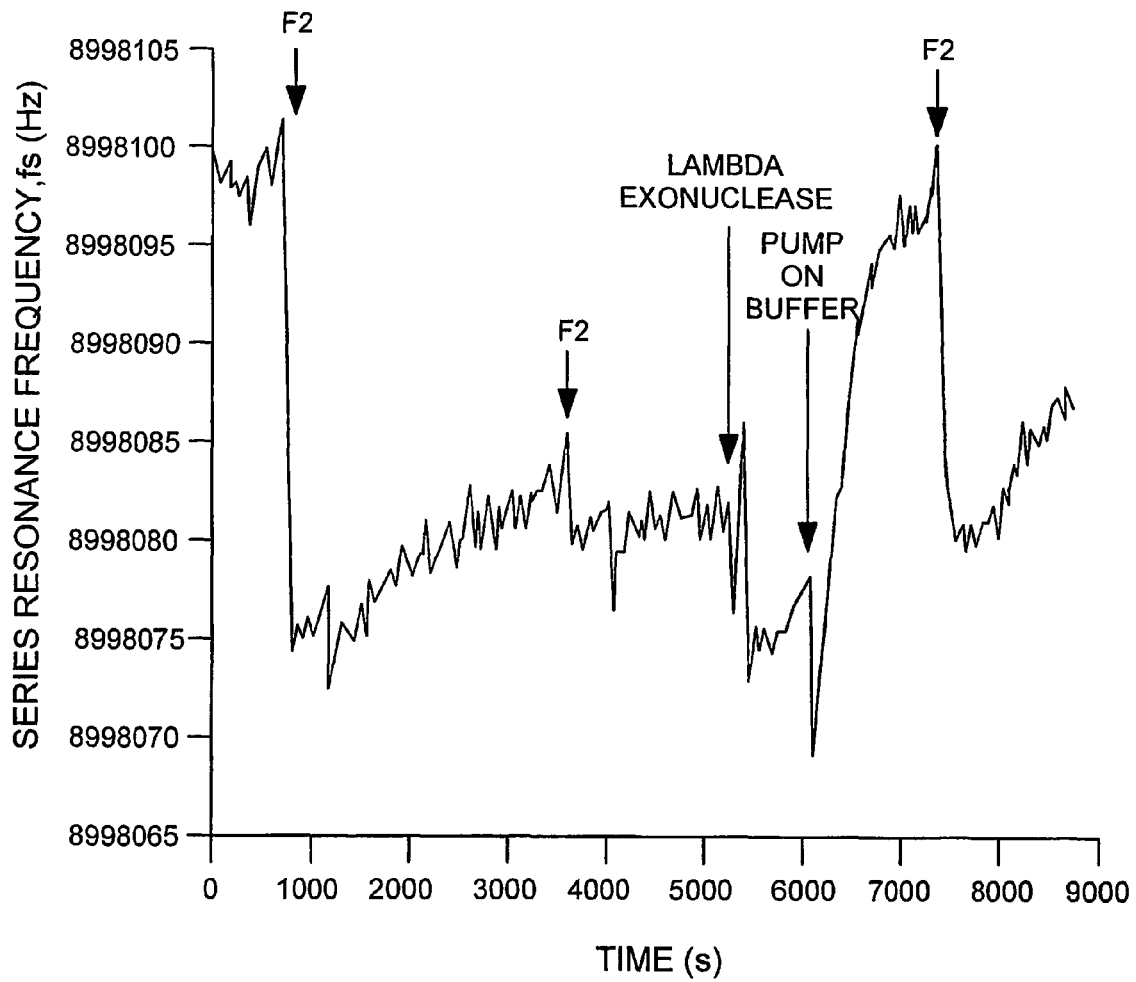
FIG. 10 illustrates the TSM frequency response for initial F1:F2 interaction, subsequent F2 injection, λ-exonuclease digestion, and final F2 injection.

FIG. 10 shows that lambda-exonuclease was successful in regenerating sites for F2 hybridization. Points of injection are indicated by arrows. Initially, the target produces a frequency shift response of −25 Hz but, with a subsequent second injection of F2, no further response was observed. This was followed with the λ-exonuclease digestion protocol. Following the observation of a stable signal at the new frequency, F2 was again injection over the TSM device and a response was observed for F1:F2 interaction by a frequency shift of −25 Hz. As expected, the TSM response indicates that the F2 target was digested and the F1 probe was left whole.

Figure 11:
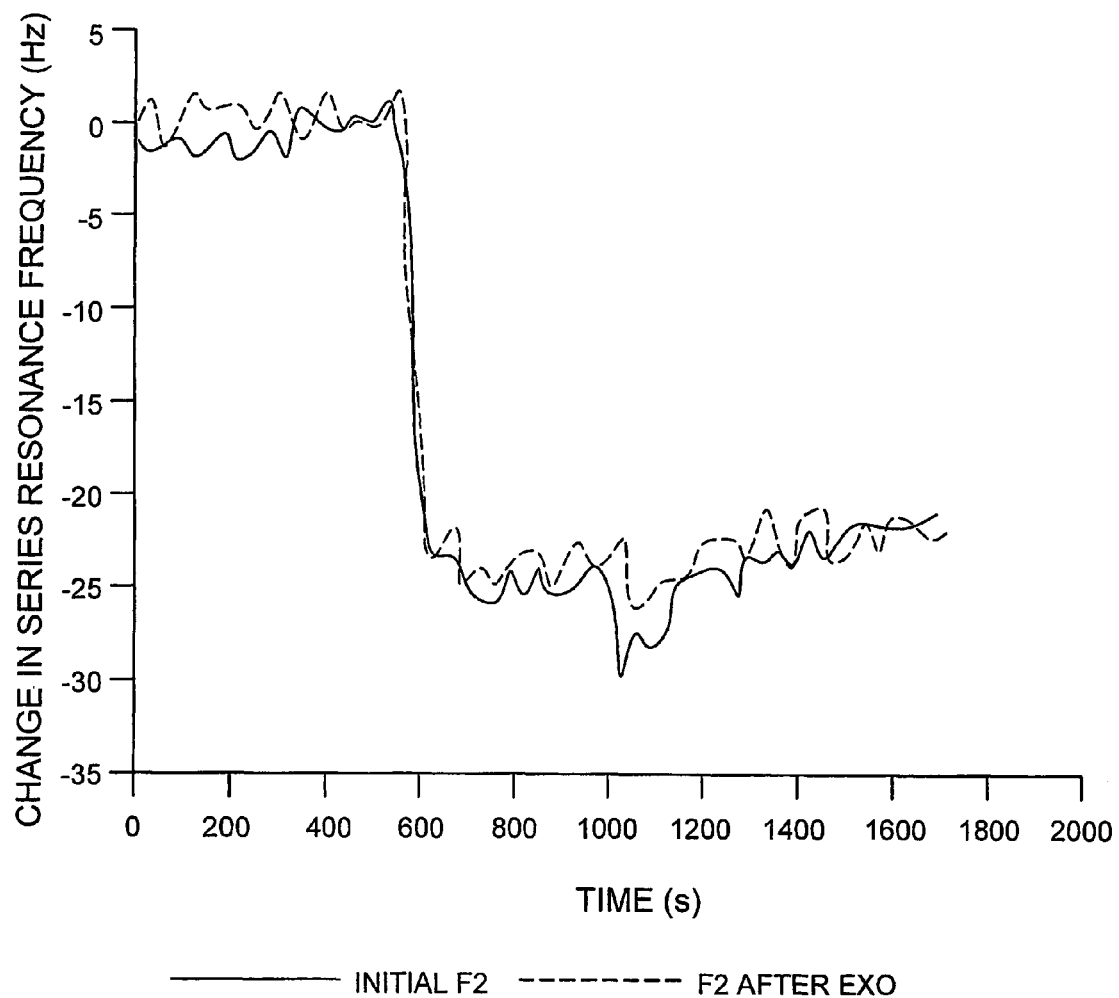
FIG. 11 shows a comparison of change of frequency versus time plots for initial F1:F2 interaction and F1:F2 interaction after lambda-exonuclease digestion.

FIG. 11 shows a comparison of TSM responses for F1:F2 initial interaction and after λ-exonuclease digestion, indicating a good correlation between the two responses. Notably, the initial F2 plot is almost superimposable on the F2 plot after lambda-exonuclease treatment. This clearly shows that regeneration of the microarray (i.e. the probe surface) was successfully achieved by λ-exonuclease digestion.

Figure 12:
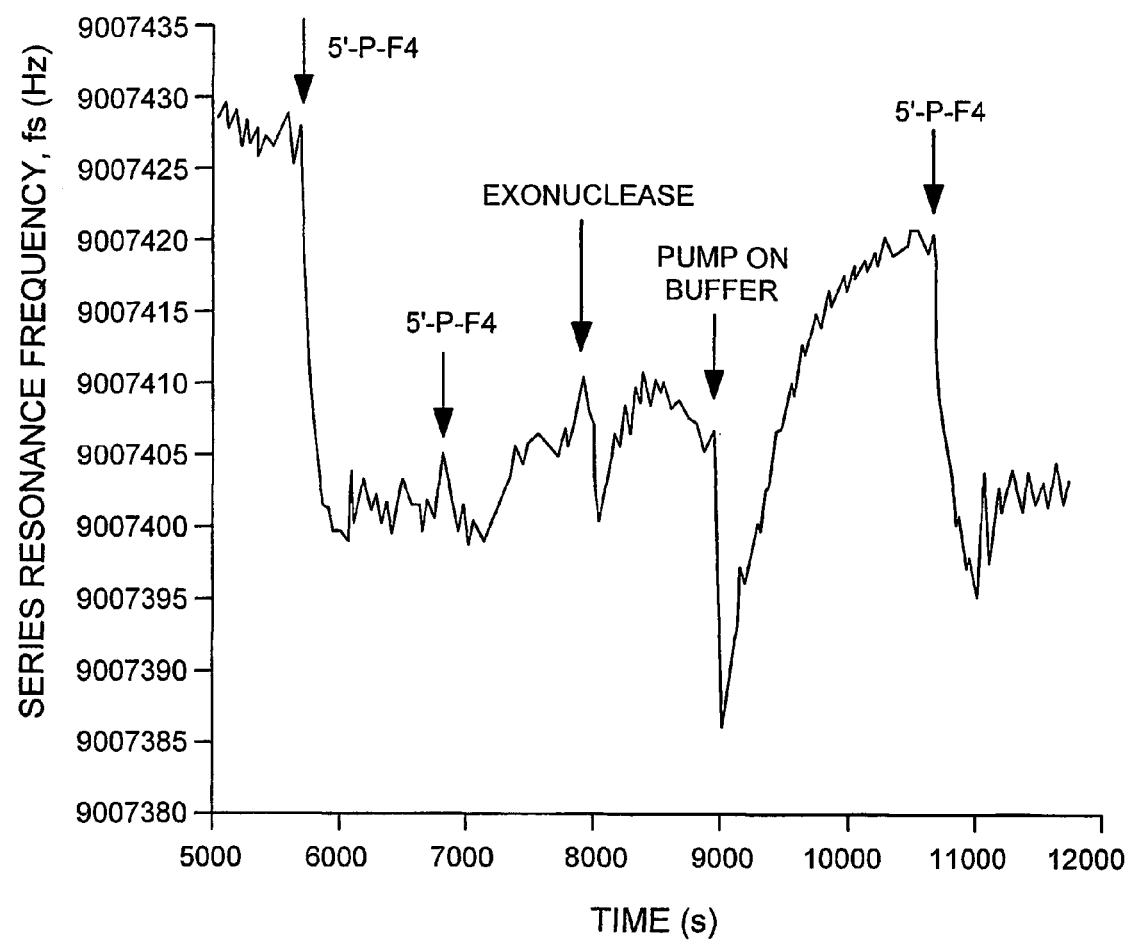
FIG. 12 shows TSM frequency response for initial F3:F4 interaction, subsequent F4 injection, λ-exonuclease digestion, and final F4 injection.

FIG. 12 is an expanded plot of the initial F3:F4 interaction followed by a second injection of F4. Points of injection are indicated by arrows. In order to establish that this was not unique to the F1:F2 system used, a second set of complementary 25-mer oligonucleotides was synthesized, and experiments were conducted using the F3 probe and F4 target with similar results. After allowing sufficient buffer washing, λ-exonuclease digestion was carried out, followed by a third injection of F3. As expected, the results are similar to the F1:F2 system: initial interaction between the complementary F3:F4 oligonucleotides results in a decrease of roughly 25 Hz; the second injection produces no appreciable response; whereas, a shift of −22 Hz is observed for F3:F4 interaction following λ-exonuclease digestion.

Figure 13:
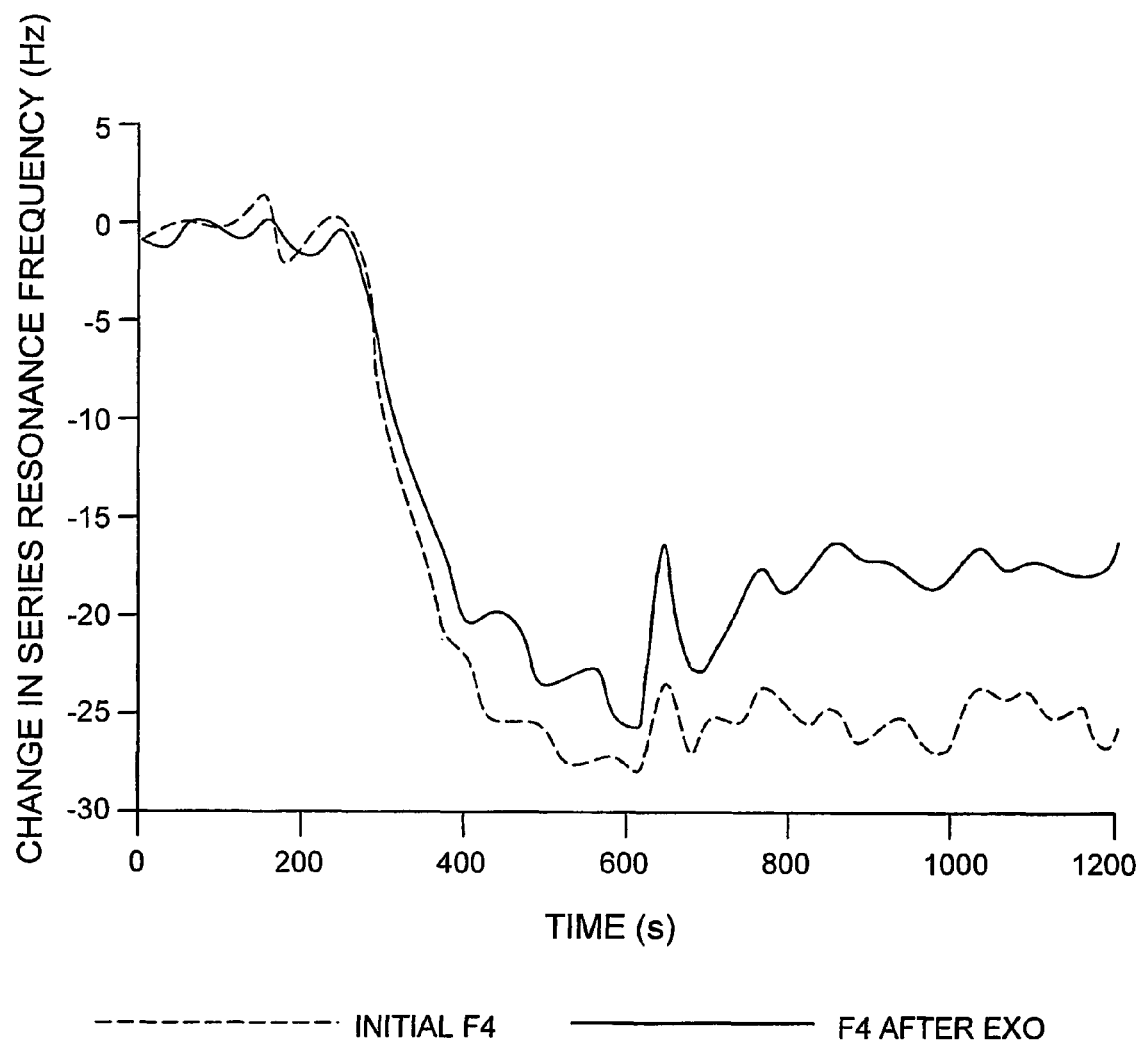
FIG. 13 illustrates the change of frequency versus time plots for initial F3:F4 interaction and F3:F4 interaction after λ-exonuclease digestion.

FIG. 13 illustrates a direct comparison of the TSM frequency responses for the initial and after digestion F3:F4 interactions.

Figure 14:
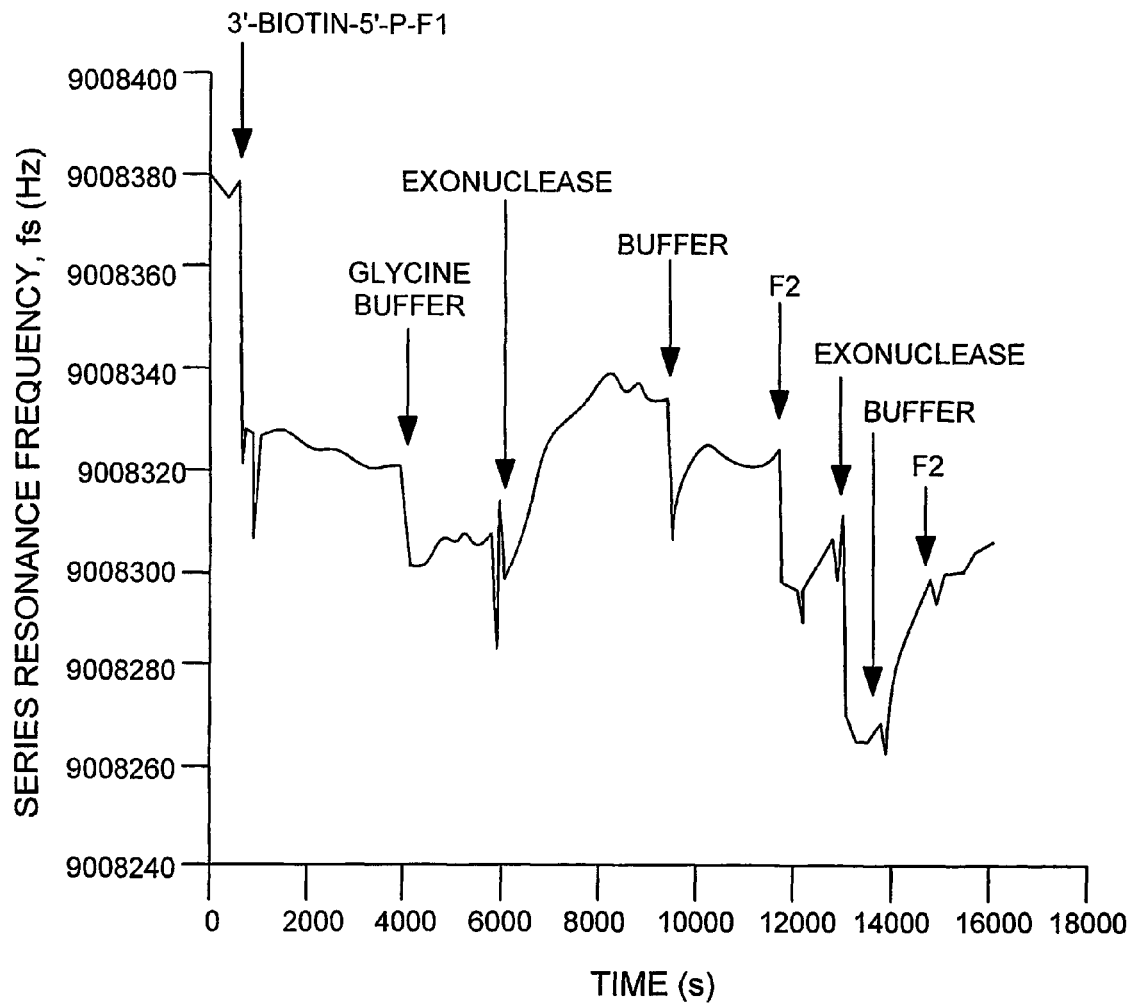
FIG. 14 shows a TSM series resonance frequency versus time plot for λ-exonuclease interaction with single-stranded 3'-biotinylated F1 followed by interaction with F1:F2 dsDNA.

FIG. 14 shows this experiment performed using an F1 probe that was 3'-biotinylated and 5'-phosphorylated. In this experiment, no initial degradation of the F1 probe was observed upon exposure to λ-exonuclease. However, after the probe was exposed to the complementary target, F2, and λ-exonuclease was again introduced to the surface, a response was observed for the digestion interaction. Upon subsequent exposure to F2, a response was no longer observed. This is in direct contrast to the results using the 5'-biotinylated F1 probe. This verifies the activity of this enzyme in two ways: 1) λ-exonuclease is most active against dsDNA and thus there was no response with λ-exonuclease and the probe-modified surface, even though a 5' phosphate was available for interaction; and 2) λ-exonuclease digests in the 5' to 3' direction, hence the null response observed for F2 injection post digestion, as the probe was selectively digested because it was 5' exposed to the bulk solution containing the enzyme.

Analysis of Radio-Labelled Oligonucleotides. The surfaces of the TSM devices were characterized using 5'-$^{32}$P-labelled oligonucleotides F1 and F2, as well as 3'-biotinylated F1. The experimental conditions differ from the TSM network analysis in that the steps were carried out according to a set time and not the re-stabilization of the frequency signal. In addition, the concentration of target F2 was varied between sets of experiments and the time of surface exposure to λ-exonuclease (i.e. time of digestion) was varied, as shown in Table 3. It was observed that both the concentration and digestion time affected the trend of calculated amounts of $^{32}$P-F2.

The first set of experiments (conditions shown in column (a) of Table 3) employed dilute concentrations (38 pmol per injection) of $^{32}$P-F2 and increased exposure time to λ-exonuclease (90 min) compared to the time (15 min) used for network analysis. The calculated amounts of $^{32}$P-F2 on the surface for the different protocols indicate that hybridization between F1 and F2 occurs. Lambda exonuclease digestion reduces the amount of F2 target on the surface to less than 1.5% the amount before digestion. Interestingly, the regeneration of F1 probe is reduced with this increased digestion time as the calculated amount of $^{32}$P-F2 for target injection after λ-exonuclease digestion (1.5% of the F1:F2 interaction) is not significantly different than that for the amount remaining after digestion alone (1.5% of F1:F2) and much lower than the amount for initial probe-target interaction of 0.78 pmol.

These data show that, although it appears that the probe surface was almost completely regenerated by target digestion, there was some inhibition to the interaction of the renewed probe with additional target. The results also indicate that there is nonspecific binding of F2 to neutravidin at the level of 5% of the F1:F2 hybridization interaction. There is also evidence of F1 interaction with a second injection of F2 subsequent to the initial F1:F2 hybridization, by an increase of 67% of the amount of F2 on the surface. Neither of these phenomena is observed by network analysis as previously shown in FIG. 8. The occurrence of a specific binding event appears to be involved in the TSM response and not merely the addition of mass to the surface (as is the case for nonspecific binding).

TABLE 3

Calculated amounts of $^{32}$P–F2 and Experimental Conditions

|  | (a) F2* (pmol) | (b) F2* (pmol) | (c) F2* (pmol) | (d) F2* (pmol) |
|---|---|---|---|---|
| Neutravidin + F2* | 0.04 | 0.06 | 0.15 | — |
| F1:F2* | 0.79 | 2.15 | 1.74 | 2.5 |
|  | 0.78 |  | 1.33 |  |
| F1:F2* + λ-exo | 0.011 | 0.16 | 0.21 | 0.84 |
|  | 0.016 |  | 0.21 |  |
| F1:F2 + λ-exo + F2* | 0.016 | 0.42 | 0.37 | 1.72 |
|  | 0.017 |  | 0.41 |  |
|  |  |  | 0.30 |  |
|  |  |  | 0.85 |  |
|  |  |  | 0.51 |  |
| F1:F2 + F2* | 0.52 | 0.72 | 0.38 | 0.96 |

(a) F2 (39 pmol), λ-exo (90 min);
(b) F2 (735 pmol), λ-exo (90 min);
(c) F2 (750 pmol), λ-exo (15 min);
(d) F2 (1490 pmol), λ-exo (15 min)

The second series of experiments (conditions shown in column (b) of Table 3) varied the concentration of target injections to 735 pmol per injection, while maintaining the digestion time at 90 min. Increasing the F2 concentration resulted in increased calculated amounts of F2 on the surface for all experiments. The relative amount of nonspecific adsorption decreased to roughly 3% of the specific F1:F2 interaction. The relative amount of digestion also increased to 7.5% from 1.5% compared to the same experiment under conditions shown in column (a) of Table 3. The amount of F1 probe available for interaction with F2 also increased by the gain in the relative amount of target interaction post digestion to 20%, compared with 1.5% under conditions shown in column (a) of Table 3. However, the results show that there is a discrepancy between the amount of target removed and the amount of probe available for hybridization. Theoretically, if 92.5% of the target was removed, then 92.5% of the original amount of probe should be available for re-hybridization. It appears that there is an inhibiting factor to this interaction. Again, there was a significant amount of F2 on the surface from a second injection of F2, 35% relative to an initial F1:F2 interaction.

The third series of experiments (conditions shown in column (c) of Table 3) differed from the (b) series in the time allowed for digestion; the time was reduced to 15 min (in accord with the original TSM network analysis experiments). The data from this series provided greater calculated amounts of F2 on the surfaces encountered for each experiment relative to the amounts calculated for the (b) series, with the exception of the last posted experiment, which decreased. The amount of nonspecific adsorption increased to 10% of the F1:F2 interaction. The amount of λ-exonuclease digestion brought the amount of F2 on the surface down to 14% of the amount prior to digestion. In addition, the amount of probe available for re-hybridization correspondingly increased to between 20 and 50% of the original amount. Even so, the amount available for re-hybridization does not equal the amount of target removed by digestion.

As well, the amount of F2 interacting from the second injection post initial F1:F2 interaction, decreased to 16% relative to the (b) series.

Noting the increase of signals with the increase of concentration between series (a) and series (b), the concentration was increased between (c) and (d), keeping the digestion time at 15 min. This provided increased overall amounts of F2 for each surface, as expected. The amount of initial hybridization increased to 2.50 pmol from an average of 1.53 pmol. The amount of target removed by λ-exonuclease digestion was 67% relative to the calculated amount for initial F1:F2 hybridization. This coincides with the amount of available probe for the re-hybridization, regaining 69% of the initial amount of F2 on the surface. The small difference between these two values is considered insignificant considering the variable of using different surfaces for each experimental datum. Again, it should be noted that there is a significant response for the second injection of F2 after initial F1:F2, but this is not observed by network analysis.

This series of experiments show that both the concentration of target and the time for digestion by λ-exonuclease are important to the regeneration of the probe surface. As the concentration of F2 is increased, the relative amount of target digestion also increases. At lower concentrations, the target is more completely removed. However, at lower concentrations, the amount of probe available for re-hybridization also decreases. When the digestion time was increased to 90 min, the amount of target digestion was, indeed, more complete, as might be expected. However, this increased time also allowed for increased interaction between the enzyme and the protein (neutravidin) layer to which the probe was attached. Thus, the amount of probe available for hybridization decreased, though, theoretically, more should be available based on the increased amount of target digested. The (d) series (conditions shown in column (d) of Table 3) incorporated both high concentrations of target and short digestion times. This resulted in an equivalent amount of target removal and probe availability. Even so, the amount of target removed was lower than the amounts for series (a) through (c). There is, however, a trade-off in the increased availability of probe. It would be beneficial to consider increasing the concentration to further test this trend.

Comparison of the set of data suggests that, with increased exposure time, the enzyme interacts with the neutravidin, forming a new protein layer, incorporating at least part of the probe layer and inhibiting interaction with target oligonucleotides. In effect, the probe layer is shielded from subsequent interaction with target molecules by adsorbed λ-exonuclease. However, high concentrations of target and short digestion times improve the effective regeneration of the probe surface.

Example 4

Analysis of Fluorophore-Labelled Oligonucleotides

Initial work with oligonucleotide probes on glass slides was performed in "macroarrays" to test the viability of the immobilization and hybridization protocols before proceeding to robotic printing of microarrays. For these experiments, the F1 probe was 5'-labelled with fluorescein and the F2 and MN-F2 targets were labelled with Alexa 546 at the 5'-end. A confocal microscope was used to scan the slides for fluorescence. On the colour scale, white represents high intensity fluorescence, then red, yellow, green and blue representing consecutively lower intensities of fluorescence.

The probe-attached slides were scanned with an excitation wavelength of 560 nm and monitored at a wavelength of 575 nm for Alexa. Because of the limitations of the confocal microscope used, the slides were scanned for fluorescein at a wavelength of 532 nm and detected at 552 nm. The appropriate wavelengths of 492 nm and 512 nm, respectively, could not be achieved. Even so, fluorescence of the fluorescein label is detectable and distinguishable from the Alexa 546 fluorescence. The probe immobilization varied, and each of the three slides displayed a slightly different intensity for the three spots where the silanized glass was exposed to the thiol- and fluorescein-modified probes. Subsequent steps with fluorescent targets indicated that there was sufficient probe immobilized to the surface. Smudging of the spots was observed and, thus, cover wells were applied to subsequent slide work.

Once immobilization was verified, the fluorophore-labelled target, F2, was applied over the areas of immobilization. It was observed that there is some interaction between the probe and target, which was presumed to be hybridization, and this was checked by comparing the response of complementary F2 and non-complementary MN-F2. Two slides, which had immobilized probe thereon were exposed to MN-F2 and F2, separately. The slide exposed to the complementary target had a significant increase in fluorescence, whereas no appreciable change in fluorescence was observed for the non-complementary interaction with the probe.

Figure 15:
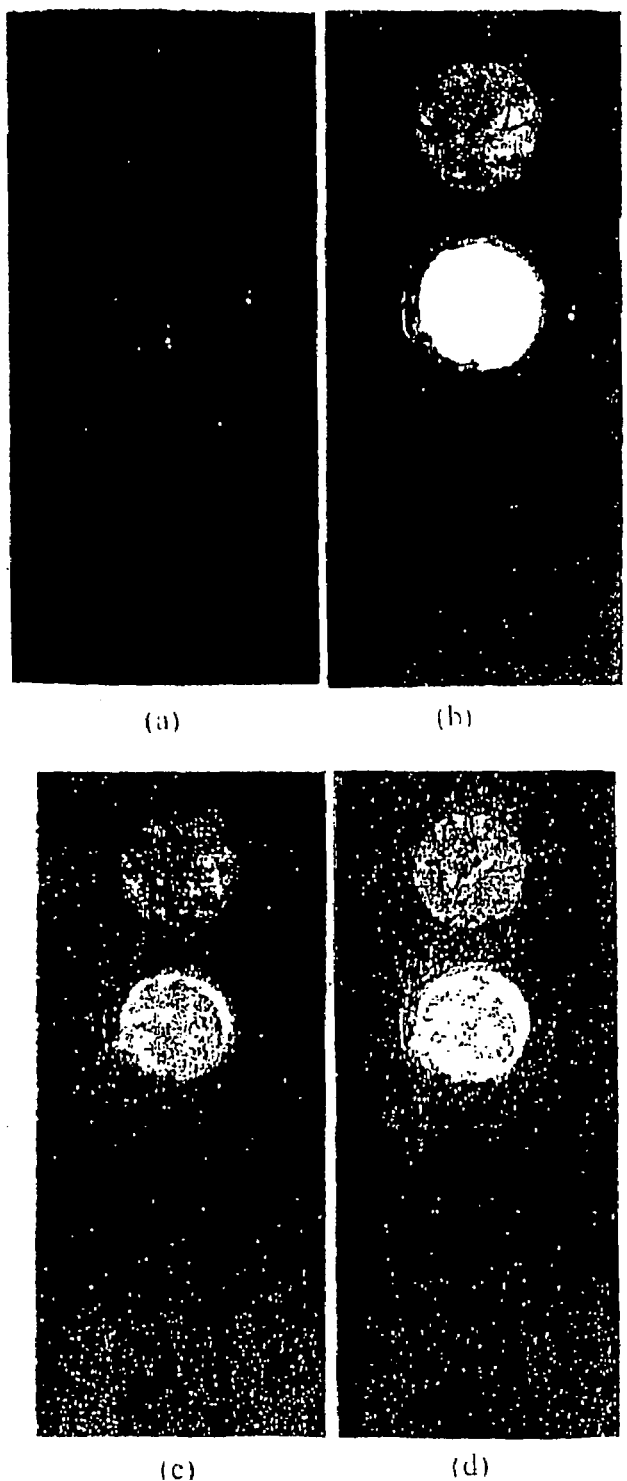
FIG. 15 illustrates λ-exonuclease activity against chemisorbed F2 (top spots) and F2 exposed to immobilized F1 (bottom spots) on slides (a) before F2 exposure; (b) after F2 exposure; (c) after λ-exonuclease digestion; and (d) after re-exposure to F2.

The next step was to test the activity of λ-exonuclease against the F1:F2. Thus, a slide was modified with probe F1 as per the protocol and exposed to complementary F2. FIG. 15 illustrates λ-exonuclease activity against chemisorbed F2 (top spots), and F2 exposed to immobilized F1 (bottom spots). At the same time, chemisorption of the target to the silanized slide was tested. The top spot indicates an area that does not have any probe and the bottom spot indicates the area having probe immobilized to it. All scans were performed using the protocol for the Alexa 546 dye, which was attached to the targets only. The first scan, shown as slide (a) in FIG. 15, represents the fluorescence of the slide before interaction with F2. As observed, both areas appear the same prior to exposure to F2. However, as shown in FIG. 15 slide (b), the amount of fluorescence for the interaction of complementary probe and target is much greater than that for mere adsorption of F2 to the derivatized glass slide. Upon subsequent exposure to λ-exonuclease digestion, there is a significant decrease in fluorescence intensities for the F1:F2 hybrids and less of a significant change for the adsorbed F2. The change in fluorescence intensity for the F1:F2 surface is expected because of target digestion and, thus, effective removal of the fluorophore. No change in fluorescence is expected for the area with adsorbed F2 (no F1) because λ-exonuclease is only active against dsDNA. The observed change may be explained by the use of buffers and washing with copious amounts of solution. It may simply be that some of the adsorbed oligonucleotide was washed from the surface during the digestion procedure. In the final step, F2 was again applied to the two areas (d). This resulted in the increase in fluorescence of both areas to close to the same intensity as for initial exposure to F2. As observed by radiochemical experiments and, to a lesser TSM analysis, it is difficult to achieve 100% digestion and re-hybridization signals.

Example 5

Enzyme-Based Regeneration of Microarray Having 3'-End Probe Attachment

A microarray is prepared using a silanized glass slides to which oligonucleotides of 15 to 25 bases in length are attached. The microarray is exposed to a test sample containing a target single-stranded DNA having a region complementary to at least one of the probe oligonucleotides. The test sample is incubated with the microarray for an adequate time period and under conditions that allow hybridization between the probe and the target. The microarray is then assessed for binding using standard methodology so that the attachment of target to probe can be quantified.

Regeneration of the microarray by removal of the target is then effected. To prepare blunt-ends on duplex regions of DNA, the microarray having duplex regions thereon is incubated with Mung Bean nuclease (Promega Corporation, Madison Wis.) in Tris buffer. A concentration of enzyme is used which is adequate to effect single-stranded termini removal, but not so high that any double-stranded DNA degradation occurs, which is a feature of this nuclease at high concentrations. Removal of protruding single-stranded termini from the probe-target hybridization product is effected, yielding blunt end duplexes (see Kowalski et al; Biochemistry 1976; 15:4457). The target strand initially hybridized to the target is considerably greater that 25 bases in length, thus the pretreatment with Mung Bean nuclease serves to reduce the overhanging single-stranded length of the target strand, beyond the duplex region. The microarray is then rinsed free of the Mung Bean nuclease using a buffer solution.

The microarray having target-probe duplexes thereon is then exposed to Exonuclease III (Promega Corporation, Madison Wis.) in Tris buffer. This enzyme digests in the 3'–5' direction in dsDNA having a blunt end (Weiss; J Biol Chem 1976; 251:1896). The enzyme activity proceeds to remove the target strand from the probe strand, and the reaction is conducted for a period of time adequate to allow complete or near complete removal of the target strand. The microarray is then rinsed thoroughly with a buffer solution to ensure removal of Exonuclease III. The microarray is thus said to be "regenerated" and is available for re-use in a subsequent assay.

The above-described embodiments of the present invention are intended to be examples only. Alterations, modifications and variations may be effected to the particular embodiments by those of skill in the art without departing from the scope of the invention, which is defined solely by the claims appended hereto.

What is claimed is:

1. A process for regenerating a microarray having a probe hybridized to a target, said probe having a surface-attached end at which said probe is attached to said microarray; said process comprising the steps of:
   a) digesting the target with a nuclease having activity for digesting one strand of a double-stranded nucleic acid in a direction starting from an end of the target opposite the end hybridized to the surface-attached end of the probe; and
   b) rinsing the nuclease from the microarray;
   wherein said microarray surface comprises a biosensor, and said biosensor is a transverse shear mode (TSM) sensor.

2. The process according to claim 1, wherein said nuclease is selected from lambda-exonuclease and exonuclease III.

3. The process according to claim 1, additionally comprising pretreatment of said microarray with a preparatory enzyme having activity for digesting single-stranded nucleic acid while leaving double-stranded nucleic acid intact.

4. The process according to claim 3, wherein said preparatory enzyme is selected from exonuclease VII and Mung Bean nuclease.

5. A regenerated microarray formed according to the process of claim 1.

6. A re-usable microarray system comprising a microarray surface, a probe nucleic acid attached to said surface in a pre-determined orientation for hybridizing to a target nucleic acid from a test sample, said pre-determined orientation selected from 3' end attachment and 5' end attachment, and a nuclease having activity for digesting one strand of a double-stranded nucleic acid in a direction starting from a free end of said target nucleic acid so as to remove a hybridized target nucleic acid from said probe nucleic acid while leaving said probe nucleic acid intact on said microarray surface; wherein said microarray surface comprises a biosensor, and said biosensor is a TSM sensor.

7. The re-usable microarray system according to claim 6, wherein said pre-determined orientation is 5' end attachment and said nuclease is lambda-exonuclease.

8. The re-usable microarray system according to claim 6, additionally comprising a preparatory enzyme for digesting single-stranded regions of said target nucleic acid.

9. The re-usable microarray system according to claim 6, wherein said probe nucleic acid is attached to said microarray surface by an attachment means selected from the group consisting of a chemical blocking group, an immobilization support, and a detection molecule.

10. A re-usable microarray kit comprising:
   a) a microarray having a surface, a probe nucleic acid attached to said surface in a pre-determined orientation for hybridizing to a target nucleic acid from a test sample, said pre-determined orientation selected from 3' end attachment and 5' end attachment; wherein the surface comprises a biosensor, and said biosensor is a TSM sensor; and
   b) a nuclease having activity for digesting one strand of a double-stranded nucleic acid in a direction starting from a free end of said target nucleic acid so as to remove a hybridized target nucleic acid from said probe nucleic acid while leaving said probe nucleic acid intact on said microarray surface.

* * * * *